(12) United States Patent
Bayon et al.

(10) Patent No.: US 11,426,106 B2
(45) Date of Patent: Aug. 30, 2022

(54) SURGICAL DRAIN

(71) Applicants:Sofradim Production, Trévoux (FR); CEA (Commissariat A L'energie Atomique Et Aux Energies Alternatives), Paris (FR)

(72) Inventors: Yves Bayon, Lyons (FR); Dagmar Guyader, Chaleins (FR); Maxime Gougis, Grenoble (FR); Mélanie Alias, Grenoble (FR); Séverine Vignoud, Bernin (FR); Frederic Bottausci, Saint Egreve (FR); Pascal Mailley, Villages du Lac de Paladru (FR)

(73) Assignees: Sofradim Production, Trévoux (FR); CEA (Commissariat A L'energie Atomique Et Aux Energies Alternatives), Paris (FR)

( * ) Notice: Subject to any disclaimer, the term of this patent is extended or adjusted under 35 U.S.C. 154(b) by 674 days.

(21) Appl. No.: 15/967,981

(22) Filed: May 1, 2018

(65) Prior Publication Data

US 2018/0338714 A1 Nov. 29, 2018

(30) Foreign Application Priority Data

May 23, 2017 (EP) .................................. 17305603

(51) Int. Cl.
*A61B 5/15* (2006.01)
*A61M 27/00* (2006.01)
(Continued)

(52) U.S. Cl.
CPC ...... *A61B 5/150992* (2013.01); *A61B 5/0022* (2013.01); *A61B 5/14507* (2013.01);
(Continued)

(58) Field of Classification Search
CPC ............ A61B 5/150992; A61B 5/0022; A61B 5/14507; A61B 5/7405; A61B 5/742;
(Continued)

(56) References Cited

U.S. PATENT DOCUMENTS 2,943,486 A * 7/1960 Osgood ..................... G01F 1/28
73/861.74
5,415,162 A * 5/1995 Casper .............. A61M 15/0035
128/203.12
(Continued)

FOREIGN PATENT DOCUMENTS

EP 2055228 A1 5/2009
WO WO 2009/044151 A1 4/2009
(Continued)

OTHER PUBLICATIONS

European Search Report for EP17305603.7 date of completion is Nov. 17, 2017 (7 pages).
(Continued)

*Primary Examiner* — Jessica R Arble
(74) *Attorney, Agent, or Firm* — Carter, DeLuca & Farrell LLP

(57) ABSTRACT

A medical drain sensor is provided located in a region of a drain tube which has turbulent or re-circulatory exudate flow. Means are provided in some embodiments to promote or enhance such flow.

16 Claims, 23 Drawing Sheets

(51) Int. Cl.
*A61M 1/00* (2006.01)
*A61B 5/00* (2006.01)
*A61B 5/145* (2006.01)

(52) U.S. Cl.
CPC ............ *A61B 5/742* (2013.01); *A61B 5/7405* (2013.01); *A61M 1/0023* (2013.01); *A61M 27/00* (2013.01); *A61M 2205/3303* (2013.01); *A61M 2205/3331* (2013.01); *A61M 2205/3334* (2013.01); *A61M 2206/20* (2013.01)

(58) Field of Classification Search
CPC . A61B 5/02444; A61B 17/02; A61B 5/02427; A61M 1/0023; A61M 27/00; A61M 2205/3303; A61M 2205/3331; A61M 2205/3334; A61M 2206/20; A61M 1/008; A61M 2205/3306; A61M 2002/0014; A61M 1/0025; A61M 2205/3382; A61M 2206/18; A61M 2206/11; A61M 2205/3386; A61M 2205/3389; A61M 1/00; A61M 2027/004; A61F 11/002; A61F 9/00781
See application file for complete search history.

(56) References Cited

U.S. PATENT DOCUMENTS

| | | | | |
|---|---|---|---|---|
| 6,340,588 | B1* | 1/2002 | Nova | G01N 35/00732 435/287.1 |
| 10,018,490 | B2* | 7/2018 | Stromsten | G01F 1/40 |
| 2008/0200791 | A1* | 8/2008 | Simpson | A61B 5/14546 600/365 |
| 2013/0304006 | A1* | 11/2013 | Toth | A61B 5/14557 604/319 |
| 2014/0058344 | A1* | 2/2014 | Toth | A61B 5/445 604/319 |
| 2014/0260667 | A1* | 9/2014 | Berkcan | G01F 1/66 73/861.28 |
| 2015/0328430 | A1* | 11/2015 | Miller | A61K 33/00 128/203.14 |
| 2016/0018347 | A1* | 1/2016 | Drbal | A61M 1/28 210/647 |
| 2016/0128583 | A1* | 5/2016 | Caron | A61B 5/02154 600/486 |
| 2018/0000999 | A1* | 1/2018 | Dolmatch | A61M 1/0017 |
| 2018/0021502 | A1* | 1/2018 | Guala | A61M 39/105 137/320 |
| 2018/0161531 | A1* | 6/2018 | Costella | A61M 16/0051 |

FOREIGN PATENT DOCUMENTS

| | | | | |
|---|---|---|---|---|
| WO | WO 2015/029039 | A1 | 3/2015 | |
| WO | WO 2016/054051 | A1 | 4/2016 | |
| WO | WO-2016054051 | A * | 4/2016 | ............ A61M 1/742 |
| WO | WO 2017/007660 | A1 | 1/2017 | |

OTHER PUBLICATIONS

European Examination Report (Communication Pursuant to Article 94(3) EPC) issued in corresponding European Application No. 17 305 603.7 dated Nov. 9, 2021, 5 pages.

* cited by examiner

SURGICAL DRAIN

CROSS-REFERENCE TO RELATED APPLICATIONS

This application claims benefit of and priority to European Patent Application Serial No. 17305603.7 filed May 23, 2017, the disclosure of the above-identified application is hereby incorporated by reference in its entirety.

BACKGROUND

This invention relates to a surgical drain for use in medical applications.

SUMMARY

A number of surgical procedures require a patient to be provided with a surgical drain to aid recovery. Surgical drains are medical devices used to provide a connection to a body cavity to allow fluids to flow out of the patient to a collection vessel. The drained fluids can include pus, blood or other fluids which gather at a wound site and could become a focus for infection or retained blood complications. The drained fluid is sometimes referred to as "exudate". The drain remains in place until the exudate flow has stopped, or has become less than a predetermined volume, for example, 25 ml per day. In order to assist the healing process, it is also known to gradually withdraw the drain from the wound by 2 cm per day, thus facilitating healing whilst maintaining the draining of the wound.

The fluid may be drawn from the wound by gravity or assisted by use of an active surgical drain utilising a vacuum pump.

Surgical drains may be made from a variety of materials to cater for a range of procedures. Typically, these are PVC, rubber or silicone formed into a tube of a diameter of 2 to 6 mm and may range in length from 50 to 100 cm.

The form of the exudate provides a useful indication of the healing process. The exudate is monitored as to its colour and consistency since that may indicate a change in the patient's condition. For example, a sudden change in the colour of the exudate to be more "bloody" and more profuse may indicate a haemorrhage. A change from thin and pink to thick and brown could indicate fecal material leaking into the wound and a colour change to green may indicate infection and the potential for sepsis.

Monitoring the exudate is therefore very important but it will also be appreciated that monitoring by nursing staff is time consuming and, between inspections, it is possible for conditions to arise which are not discovered for many hours until the next scheduled inspection takes place. This delay may have serious consequences for the patient, as remedial treatment to correct a post-operative condition, such as an infection, is delayed.

Another issue experienced, is that the exudate flow may fall for reasons not associated with there being less material in the wound to be drained. For example, the drain may become clogged, and the flow reduced, even though the wound still needs draining. This can lead to the drain being removed too early from the patient.

It has been proposed to provide drains with sensors to monitor the exudate flow. However, such sensors are sometimes inaccurate as a result of becoming "fouled" by materials in the exudate.

The present invention arose in an attempt to alleviate or mitigate these and other problems, and came from a realisation by the inventors, that by placement of sensors in an area of re-circulatory flow there could conferred a number of advantages. These include reducing the fouling of the sensor surface, and since the area of recirculation provides a mixing zone, a more accurate reading of the exudate composition. A further realisation by the inventors, was that the re-circulatory flow of the exudate could be generated or enhanced by provision of features to affect the exudate flow.

According to the invention, there is provided a medical drain comprising a tube within which, in use, exudate flows from a surgical site, a sensor located in the drain to be exposed to exudate flow and which sensor being located in a region of re-circulatory exudate flow.

By locating the sensor in a region of re-circulatory flow, the sensor is exposed to continually moving exudate which ensures that the exudate particles do not settle onto the surface of the sensor thus preventing fouling. Furthermore, the re-circulatory flow provides mixing of the exudate to allow a better reading of its composition to be provided by the sensor.

In an embodiment of the invention, the sensor is located, at least in part, within a vertical limb of a "T" shaped section of the drain. For example, the sensor may be located within the vertical limb of a Luer lock. The exudate in flowing across the junction of the vertical limb of the T will exhibit re-circulatory flow which then passes over the sensor. The sensor may be attached to the tube wall of the vertical limb or mounted onto a support member which, preferably, is made removable to allow the sensor to be conveniently replaced.

The re-circulatory flow may be also enhanced by features mounted to, or formed on, the inner surface of the drain. For example, the surface of the drain may be roughened or provided with projections to provide flow modifying means.

Preferably, the flow modifying means is a turbulator or a series of turbulators. In a preferred form these comprise projections which extend inwardly towards a central longitudinal axis of the tube forming the drain.

The size of the projection that is preferred will depend on the diameter of the tube but a preferred ratio is a projection by one quarter of the tube diameter.

Preferably, the turbulator comprises an inclined face which in a preferred form provides a turbulator which extends in a direction of flow to form a wedge shape in section. The length of the wedge shape will depend on the desired result but a dimension which extends in the flow direction amounting to substantially 50% of the diameter has been found to be advantageous.

The angle of inclination of the inclined face relative to the wall of the tube may be varied as required. A preferred range is 14.5 to 45 degrees with a range of 14.5 to 30 degrees being most preferred.

The sensor may be mounted on an inner surface of the drain wall or may be mounted on a turbulator. Particularly, where the sensor is mounted on the turbulator the sensor may be mounted on the inclined face. The preferred position will be at the innermost end that is to say the end of the face closest to the longitudinal central axis of the drain.

A wide range of sensors may be used with the preferred type being a microelectrode sensor.

By re-circulatory flow, it is meant a flow which includes vortices or other non-laminar flow.

BRIEF DESCRIPTION OF THE DRAWINGS

Specific embodiments of the invention will now be described with reference to, and as illustrated by, the accompanying drawings of which.

DETAILED DESCRIPTION OF EMBODIMENTS

Figure 1:
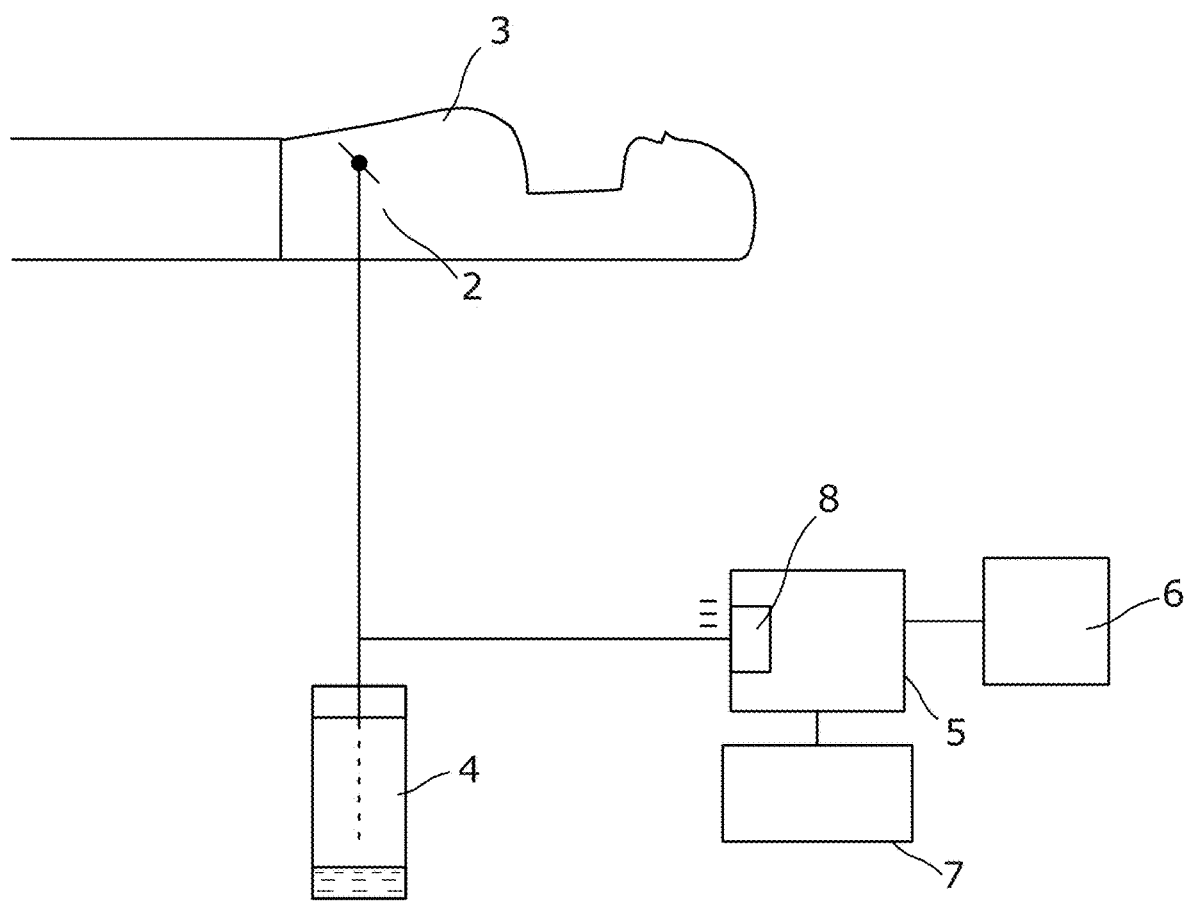
FIG. 1 shows a schematic overview of a system for monitoring a surgical drain in accordance with the invention located in the wound of a patient.

As is shown in FIG. 1, a system 1 for monitoring a surgical drain comprises a drain 2 located in a wound of a patient 3, an exudate collection vessel 4 into which the drain conducts the exudate drained from the patient and a monitoring system 5.

The monitoring system 5 includes an output device 6, a keyboard input device 7 and a set of input ports 8. The output device 6 includes a screen and an audio alarm output. The monitoring system 5 is a microprocessor based system operating under software control to provide blocks of functionality. Broadly, the functions include a means to monitor the exudate flow from a drain sensor located in the drain to provide an indication of the flow conditions and to provide an alarm if those conditions indicate that the patient requires attention from nursing staff.

Figure 2:
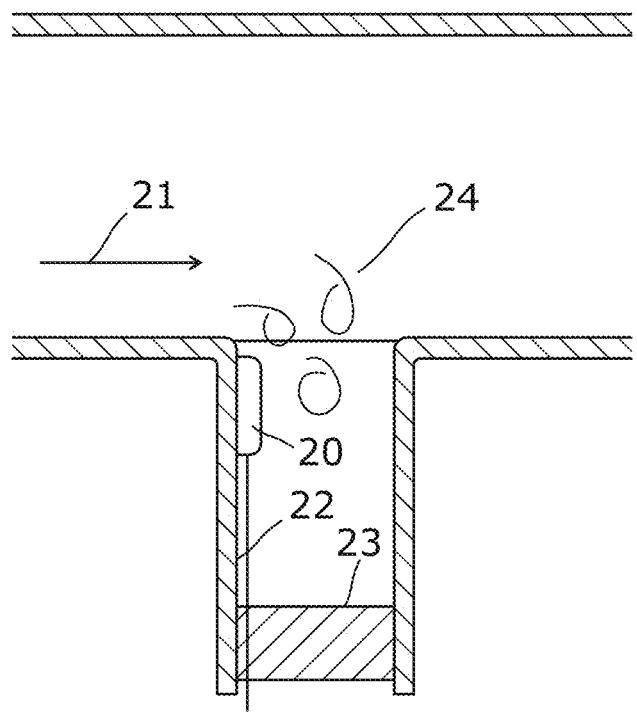
FIGS. 2 to 9 show cross-sectional views of various embodiments of surgical drains including drain sensors for use in the system shown in FIG. 1.

FIG. 2 shows a first example of a drain sensor 20 used in an embodiment of the invention. The drain sensor 20 is located in the immediate vicinity of a branch in the drain 2. The branch is a T-shape Luer-lock fluidic connector known in the art but the invention will also be applicable to other drain shapes and connections, for example, those traded as Polymedic or Pajunck. The direction of exudate flow is indicated by arrow 21. The drain sensor 20 is provided with a communication cable 22 which passes through a seal 23 and hence onwards to be coupled to the input ports 8 at the monitoring system 5. It will be appreciated that the sensor output may be provided in a manner compatible with a number of data communication protocols. Whilst depicted in this embodiment, as a data over cable link, the drain sensor may be made wireless to operate, for example, in accordance with Bluetooth or other protocols. Power for the sensor operation may be provided over the cable or by use of a battery or wireless power transmission.

The drain sensor 20 is fabricated as a series of microelectrodes. Microelectrodes are used in the medical field to perform bioelectroanalysis. They comprise electrodes of a diameter below 100 μm and more particularly in the range of 1 to 20 μm. A suitable device is an array of 10 to 20 electrodes although the array may be formed of any number.

The drain sensor 20 is depicted in FIG. 2 as a discrete component fixed to the inner wall surface of the drain. In other applications, it will be possible to form the sensor onto the wall of the drain by a deposition technique or printing.

As shown, the drain sensor 20 is placed in a region of re-circulatory flow in the vertical branch of the "T". This advantageously, removes fouling from the sensor surface to ensure that the reactive surface is exposed to "fresh" exudate. The re-circulatory flow is shown by arrows 24

Figure 3:
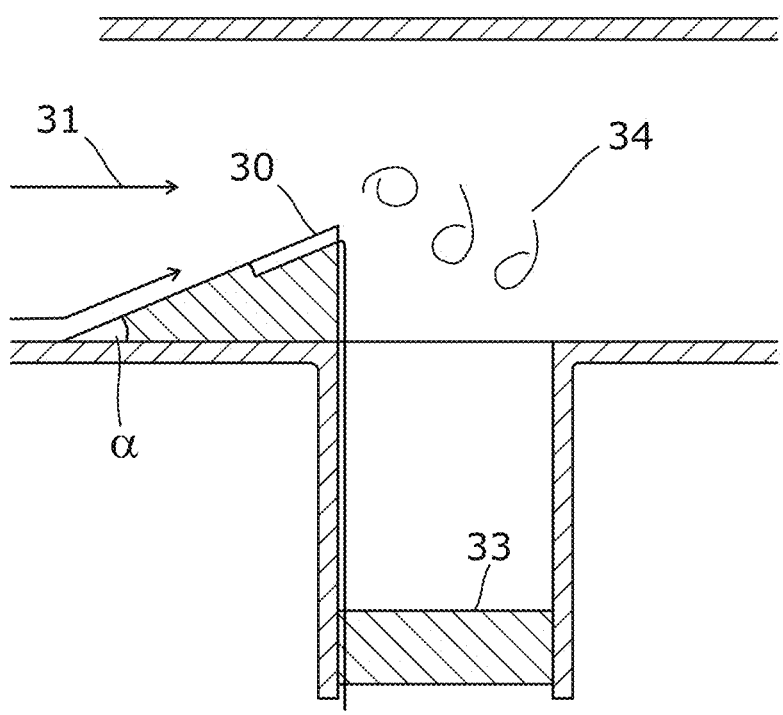

FIG. 3 illustrates a second embodiment. In this the re-circulatory or turbulent flow is enhanced by the use of a ramp with the drain sensor 30 formed in the surface of the ramp 30a. The ramp 30a provides a restriction which accelerates the exudate flow and the sharp edge 30b promotes turbulent or re-circulatory fluid flow 34 which acts as before to clean the sensor. In this case, the drain has a diameter of 4 mm and the ramp rises from the inner wall of the drain to a height of 1 mm over a length of 2 mm. The inclined face of the ramp is at an angle α to the wall of the tube which, in this case, is 30 degrees.

Figure 4:
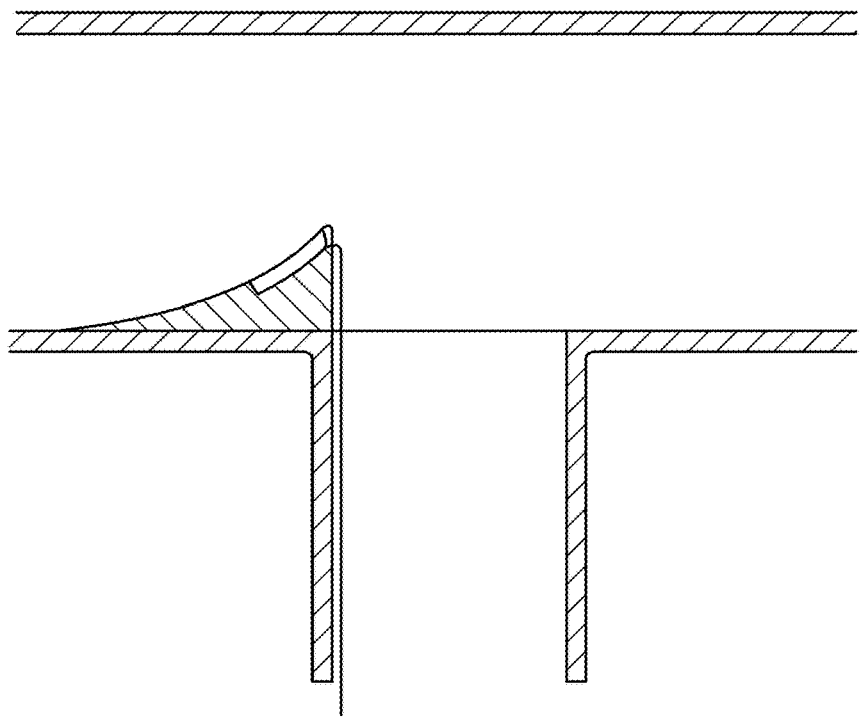

It will be appreciated that the ramp may be provided with different angles of slope a and different lengths. Angles in the range 14.5 to 45 degrees and a preferred range of 14.5 to 30 degrees have been found to provide advantageous results. The angle of slope may be a constant angle or varying. FIG. 4 shows an embodiment in which the angle of slope increases to provide an inclined face which, in section, describes a curve.

Figure 5:
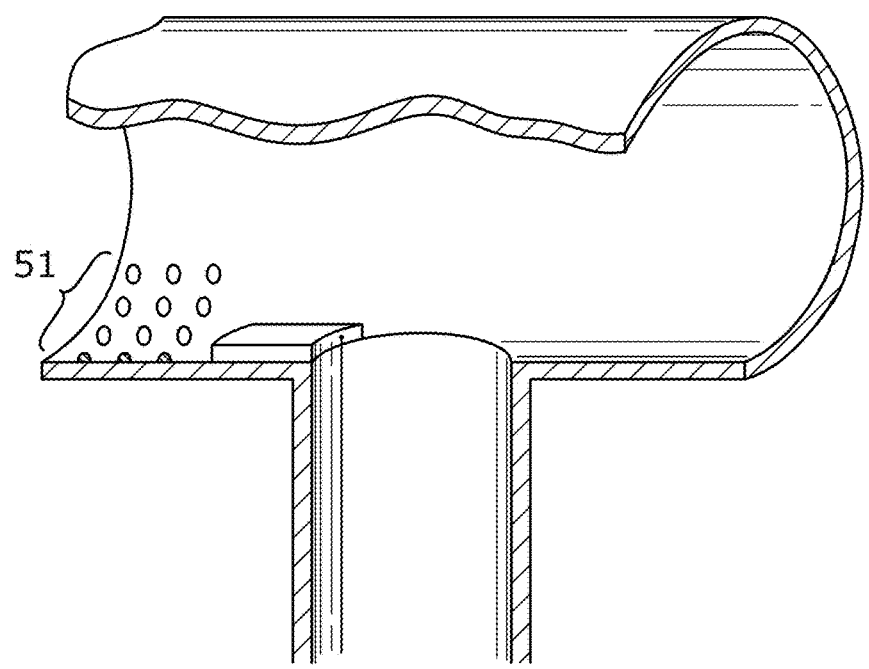

The purpose of the ramp is to enhance or promote the re-circulatory or turbulent flow. This may also be achieved by the use of "turbulators" upstream of the sensor. The turbulators may have a variety of shapes to provide this function. For example, the turbulators may be ribs, pips or depressions, roughened or textured surface or combinations thereof formed in or on the drain tube upstream of the sensor. In FIG. 5, a series of hemispherical raised portions or "pips" 51 are formed in the drain wall with the sensor 50 being positioned directly on the wall. It will be appreciated that the turbulators may be used in conjunction with a ramp as shown in the earlier embodiments or other features designed to modify the exudate flow.

The turbulators are described in these embodiments as passive. That is to say, they modify the exudate flow by means of their shape alone. However, it will be possible to augment this action by making the turbulators "active". This may be achieved by, for example, employing elements which may be made to vibrate or to inject acoustic waves, heterogeneous fluids, bubbles or the like. It will also be appreciated that the sensor elements themselves may be configured as, or incorporated with, vibrating elements to clean the sensor by causing vibrations to make fouling materials fall away from the sensor surface. These active elements may be used alone or combined with the passive turbulators.

In the above described embodiments, one drain sensor is shown. It will be appreciated that more than one sensor may be provided. Advantageously, a further sensor or sensor may be positioned downstream or upstream of the first. This is advantageous since it will provide further information of the rate of flow of the exudate.

Figure 6:
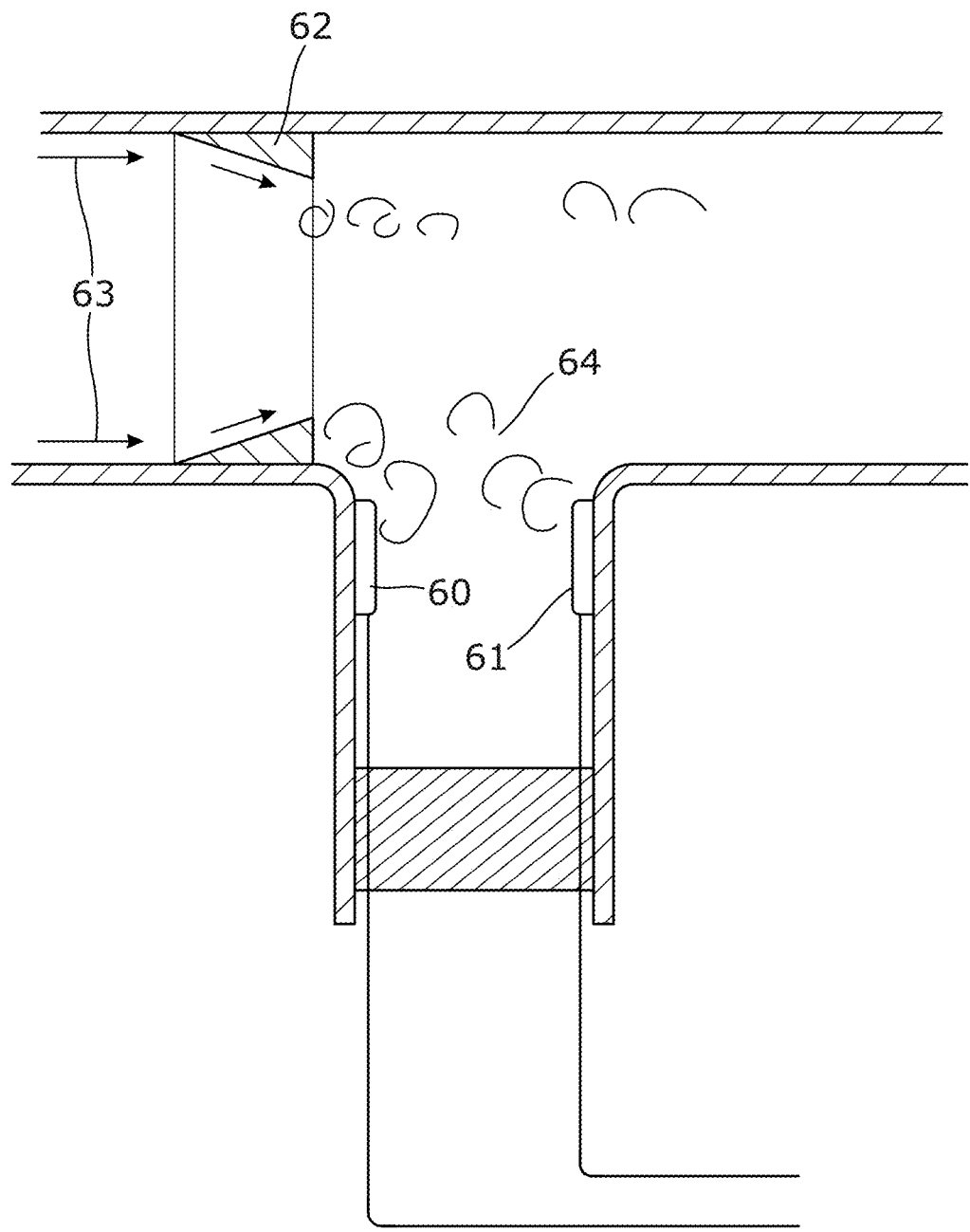

FIG. 6 shows a further embodiment similar to that of FIG. 2 in which a second sensor 61 is provided at the other side of the T branch opposite the first sensor 60. In this embodiment, a turbulator 62 is provided as a rib with a ramp-like cross-section which extends circumferentially about the inner wall of the drain. This modifies the exudate flow 63 to provide a re-circulatory or mixing flow 64 over the two sensors.

Figure 7:
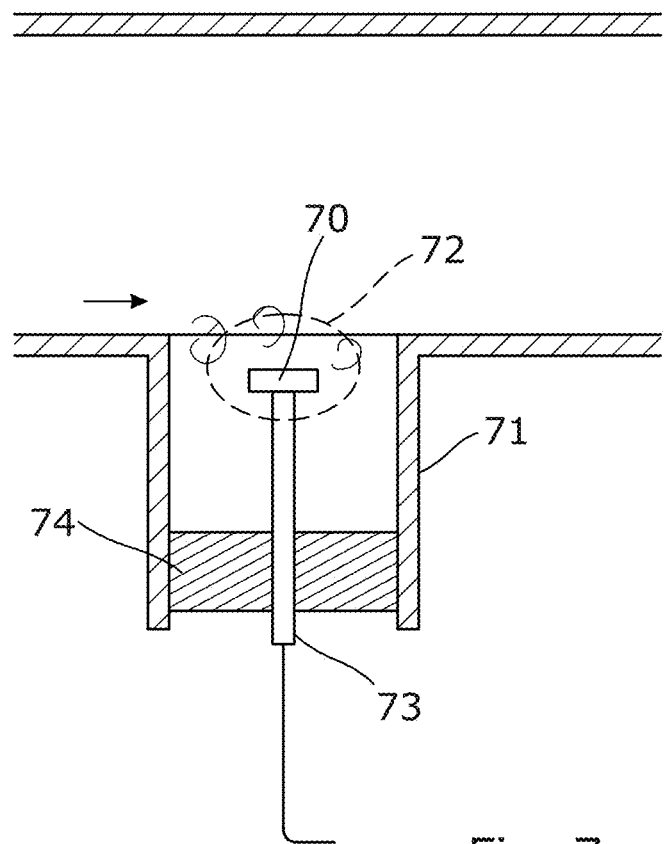

In FIG. 7, we have a further embodiment in which the drain sensor 70 is located in the vertical branch 71 of the "T" in a region or zone of recirculation 72 indicated in broken outline which is produced as the exudate flows across the junction. In this embodiment, the sensor 70 is fixed on a post 73 which extend through the seal 74. This permits repositioning of the sensor and also enables the sensor to be easily replaced in the event of failure, for maintenance or for substitution of another sensor type. In alternative embodiments, the sensor and post may be integrated with the seal to provide a removable cap for ease of replacement.

Figure 8A:
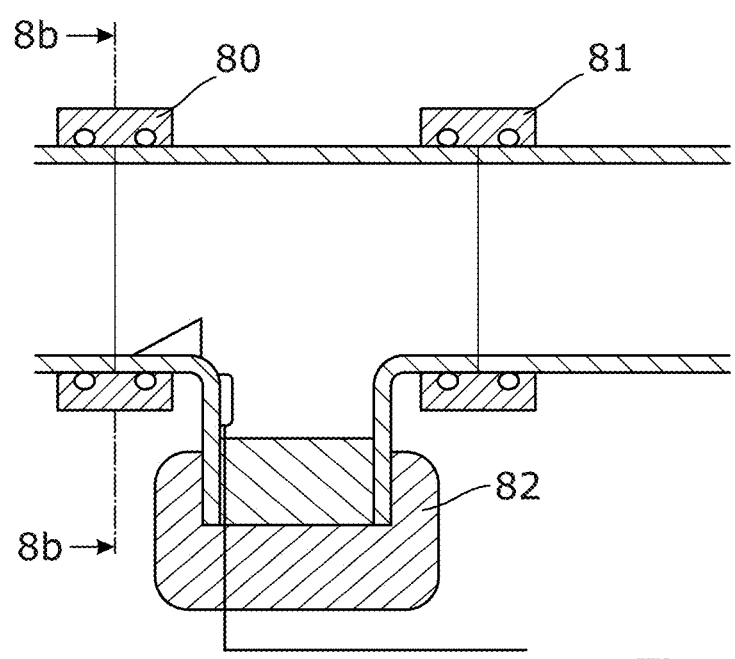
Figure 8B:
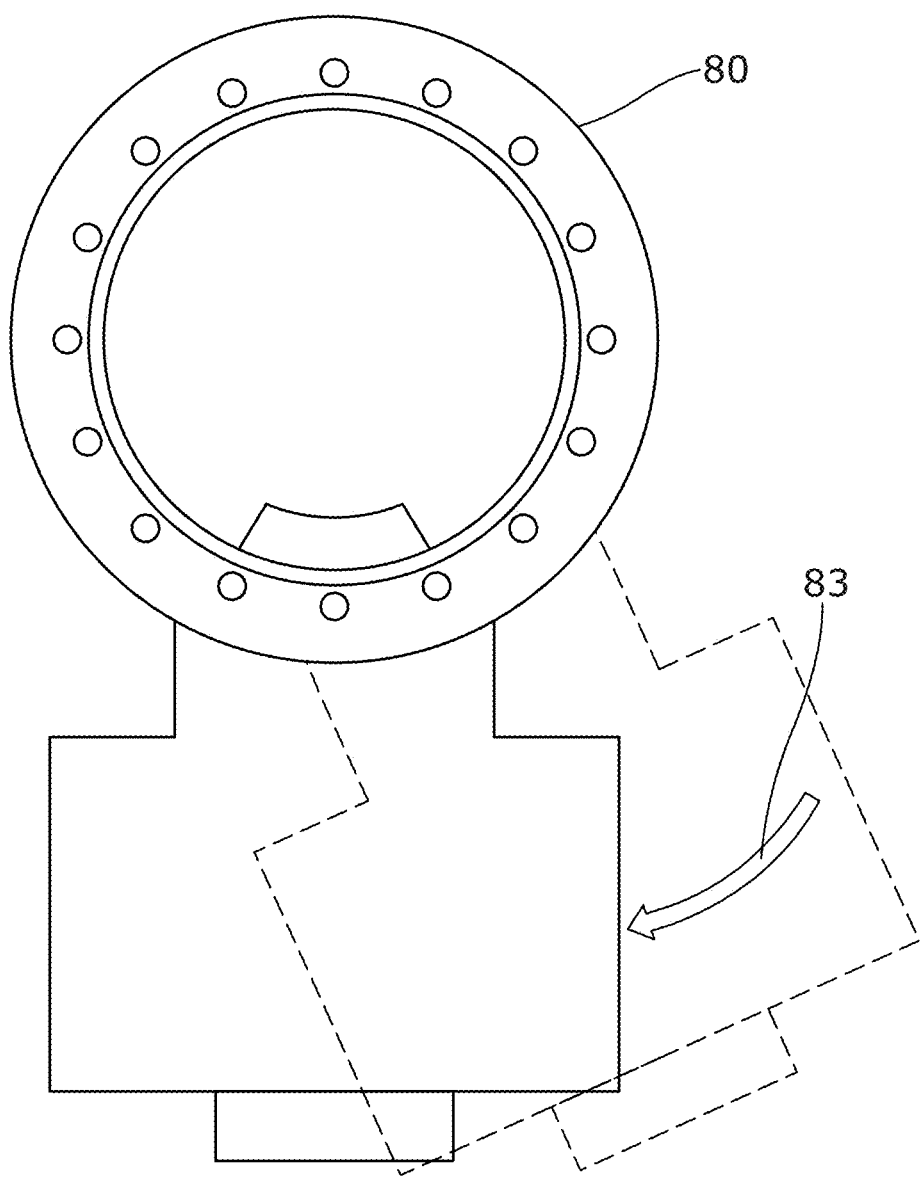

FIGS. 8a and 8b show a yet further embodiment. Where the sensor's position relative to the exudate flow is sensitive to movement of the drain, for example, where the passage of the exudate over turbulators or the branch of a drain "T" induces the re-circulatory or turbulent flow, the orientation of the drain may become important. As will be appreciated, as the drains are flexible, they are able to move and twist affecting the sensor's orientation which may not always be detected by medical staff. In this embodiment, the Luer-lock is gimballed such that the "T" remains correctly orientated. A sealed joint is provided 80, and 81 either side of the "T". Each sealed joint is provided with bearings and a seal to provide a joint which seals yet permits rotational movement. A weight 82 is provided on the vertical branch to enable the lower branch to swivel under gravity if the drain is moved, as is shown by FIG. 8b, where the Luer-lock moves in the direction of arrow 83 from a displaced position shown in broken outline to a rest position.

In alternative embodiments, the sensors may be provided at a number of positions about the inner periphery through 360 degrees such that any orientation of the drain will result in exudate passing over a sensor.

It will be appreciated that the type of turbulator and the position of the sensor will vary according to the drain parameters and the particular surgical application. The vorticity induced by a particular size and configuration of ramp has been found to increase as the drain diameter is reduced. However, as the drain diameter is reduced then the possibility of a blockage occurring increases. Accordingly, the preferred ramp height has been found to be ¼ of the diameter of the drain. (Nevertheless, ramp height slightly bigger or smaller can also give satisfactory results, such as ⅕ or ⅓ of the diameter of the drain.) The angle that the ramp makes with the drain wall has been found to give good results in the range of 14.5 degrees to 45 degrees with a preferred range being 14.5 to 30 degrees.

Each of the above described embodiments may be combined with the others as required.

The way in which the sensor or sensors locations may be perfected will now be described with reference to a number of practical modeled examples.

Example 1

Figure 9:
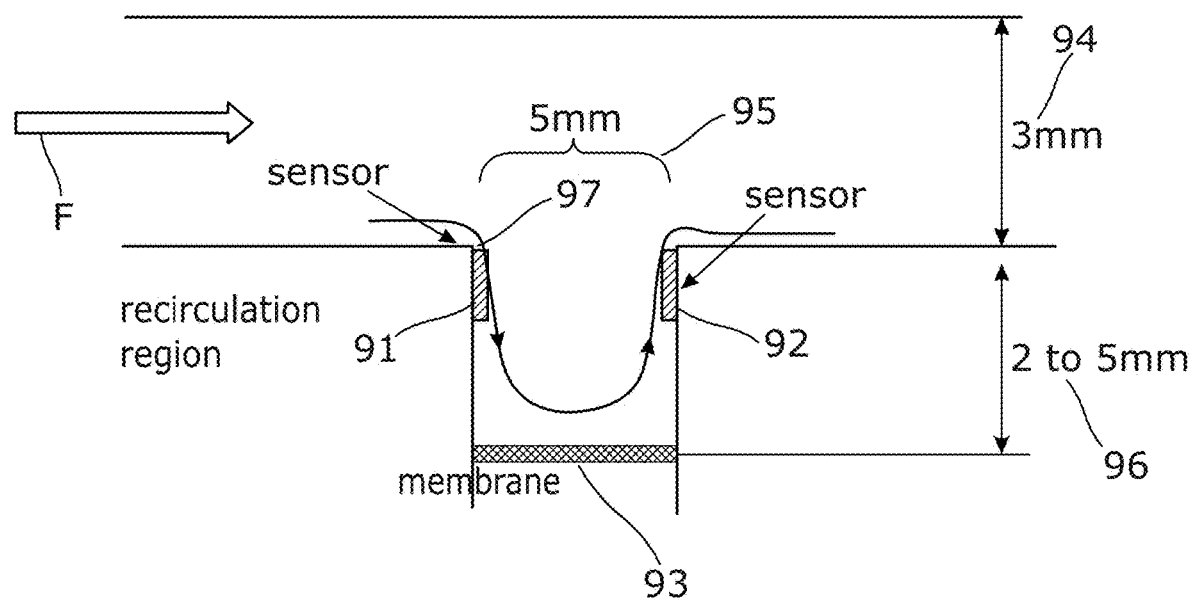

In FIG. 9, the sensors 91, 92 are located into a T connection made from any leak free connector like Luer-lock, Polymedic, Pajunk etc. . . . for instance. A porous membrane 93, for air extraction, is placed at the bottom of the vertical branch of the "T" in order to clear the trapped air during the filling of the drain. The vertical branch may be referred to as the cavity.

The sensors are positioned away from the membrane since there is a dead volume at this location where flow, and also vorticity, will be at a minimum. The sensors 91 and 92 are located at the junction in the T where the fluid circulation is maximum. At this position, the sensor will be in contact with renewed fluid and the measurements of the exudate will be more reliable. The fluid circulation is quantified by the vorticity which is a pseudo vector field that describes the local spinning/motion of fluid near some point. The drain diameter 94 is 3 mm and the diameter 95 of the vertical limb of the "T" is 5 mm. The "depth" of the vertical limb 96 is varied between 2 to 5 mm.

In example 1, the flow was modelled using a commercial flow modelling software package (called COMSOL, Multiphysics available from COMSOL, Inc.) to determine the optimum position for placing the sensors. The resulting plots of simulated flow are shown in FIGS. 10a-10d. The fluid for the simulation was water but this will adequately model exudate (since water and exudate have a similar viscosity) and the flow rates were 25, 50, 100 and 200 ml/24. The grey scale is the component z of the vorticity (1/s). The black lines represent the streamlines. The flow is mostly laminar.

For higher flow rates for high flow, small re-circulations can appear at the corner 97 of FIG. 9.

Figure 11:
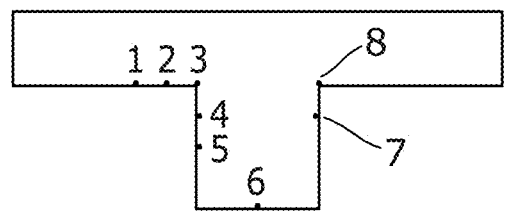
FIG. 11 is an explanatory diagram to illustrate potential positions of sensors in a "T" shaped drain shown in cross-section in accordance with the invention.
Figure 12:
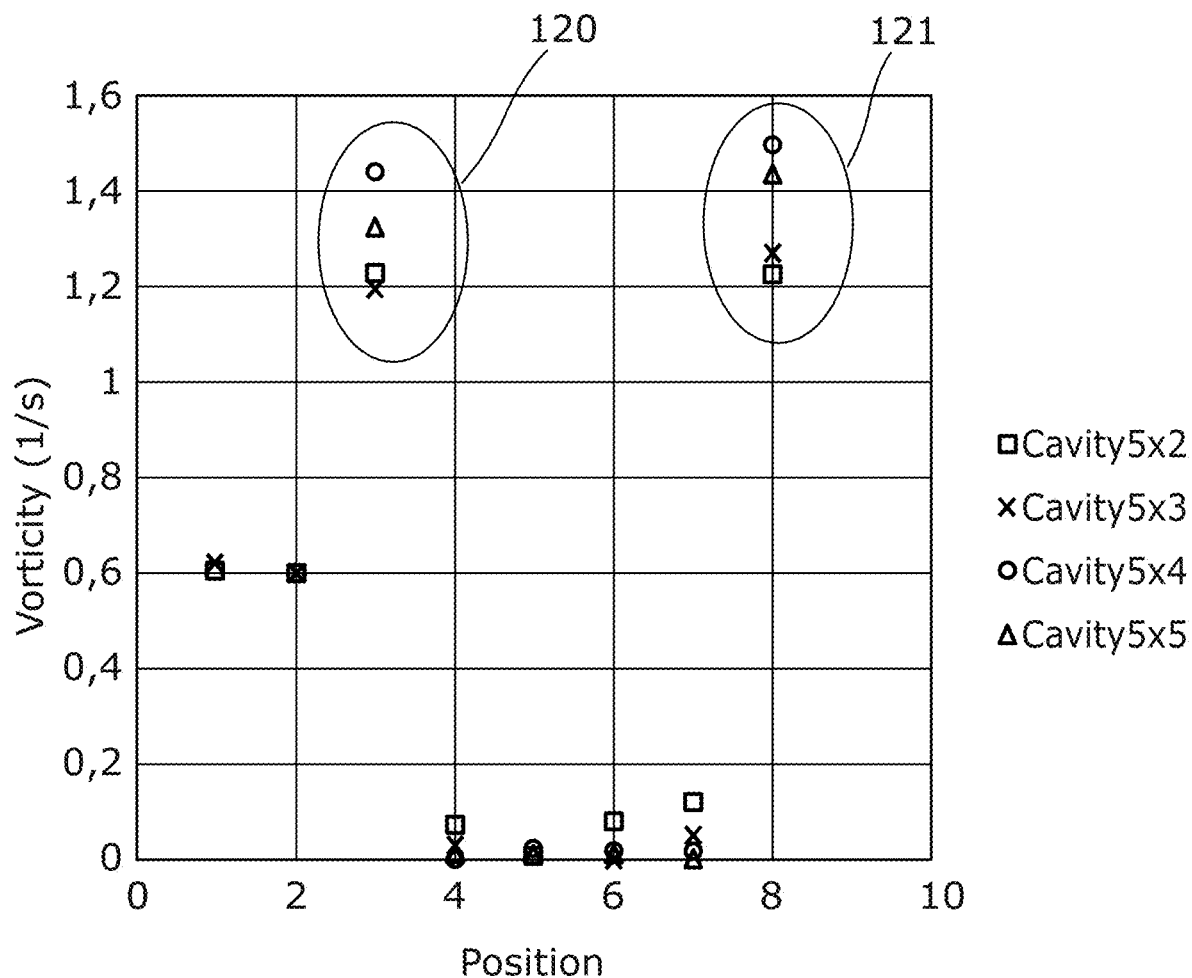
FIG. 12 shows a graph of the vorticity of the modelled flow of exudate for the various positions of sensors as shown in FIG. 11.

The preferred location of the sensors 91, 92 was found using numerical simulations for varying depths 96 of the vertical limb of the "T", 2 mm, 3 mm, 4 mm and 5 mm with the diameter of the "T" being held at 5 mm. The simulations were run for a number of positions, 1 to 8, shown in FIG. 11 and the results are shown in FIG. 12. It will be seen that the maximum vorticity is to be found at positions 3 and 8 as shown by plots 120 and 121. Hence, the sensors 91 and 92 are positioned as shown in FIG. 9 for best results.

The results 120 and 121 shown in FIG. 12 also show that a depth of 4 mm provides the best output for a diameter of 5 mm of the vertical limb.

Figure 13:
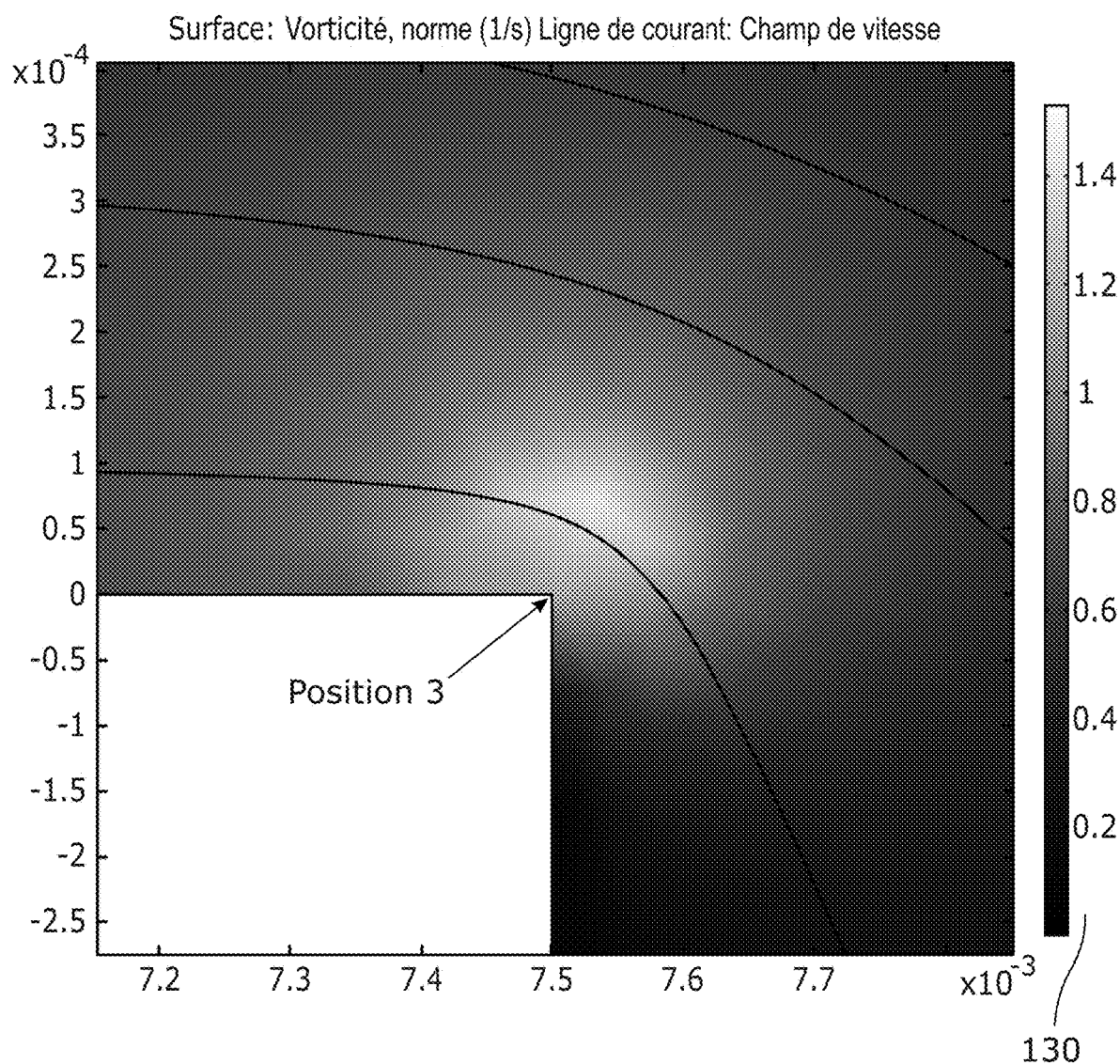
FIG. 13 shows how the vorticity varies at a position close to the vertical limb of the T shaped drain with higher levels of vorticity indicated by lighter shading.

FIG. 13 shows a close-up of the flow at the edge of the cavity (position 3) and the grey scale of the shading shows most vorticity at this region. The vorticity scale 130 ranges from below 0.2 to just over 1.4 $s^{-1}$.

Figure 10A:
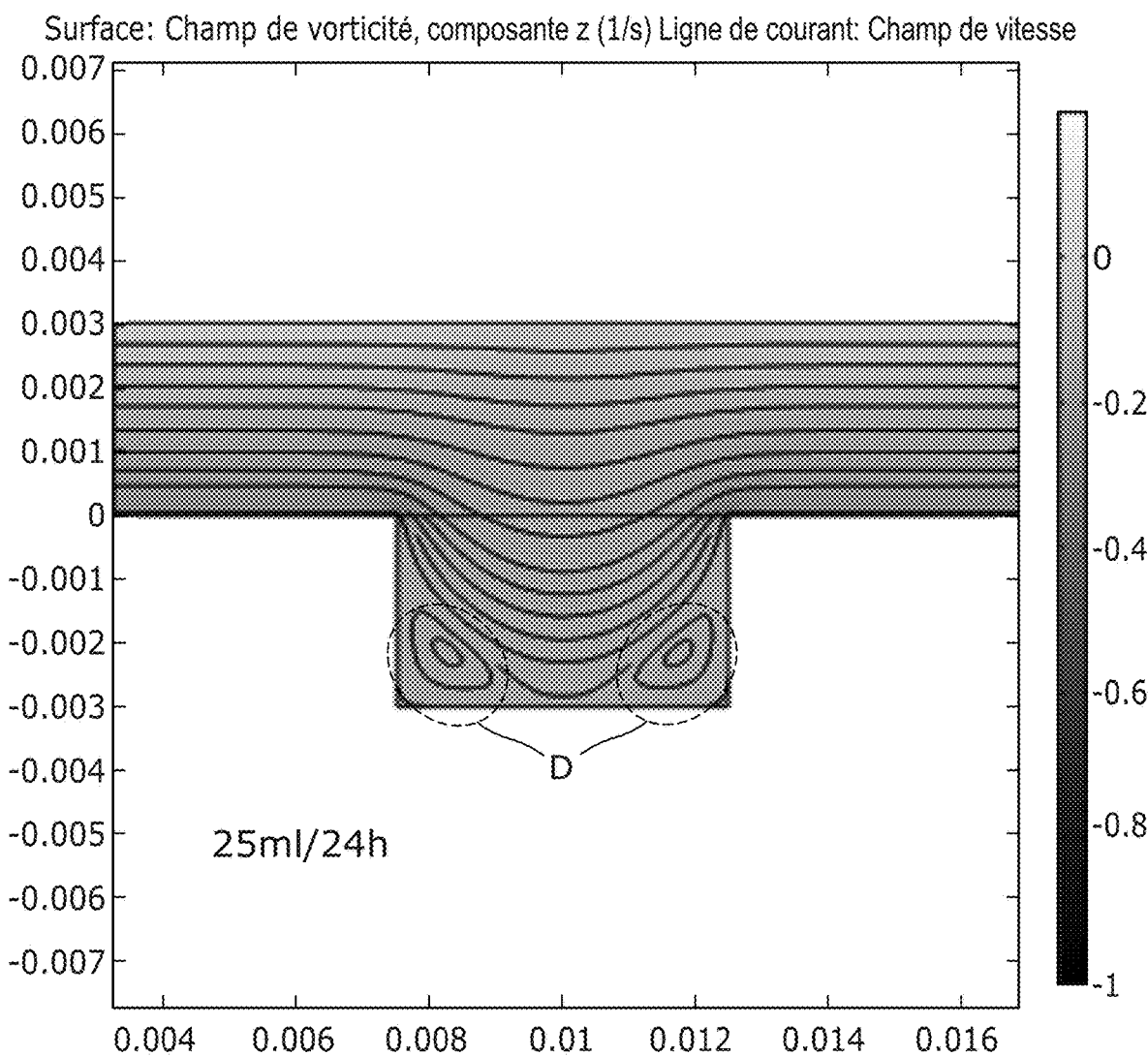
FIGS. 10a-10d show a series of flow simulations for a drain in accordance with the invention.
Figure 10B:
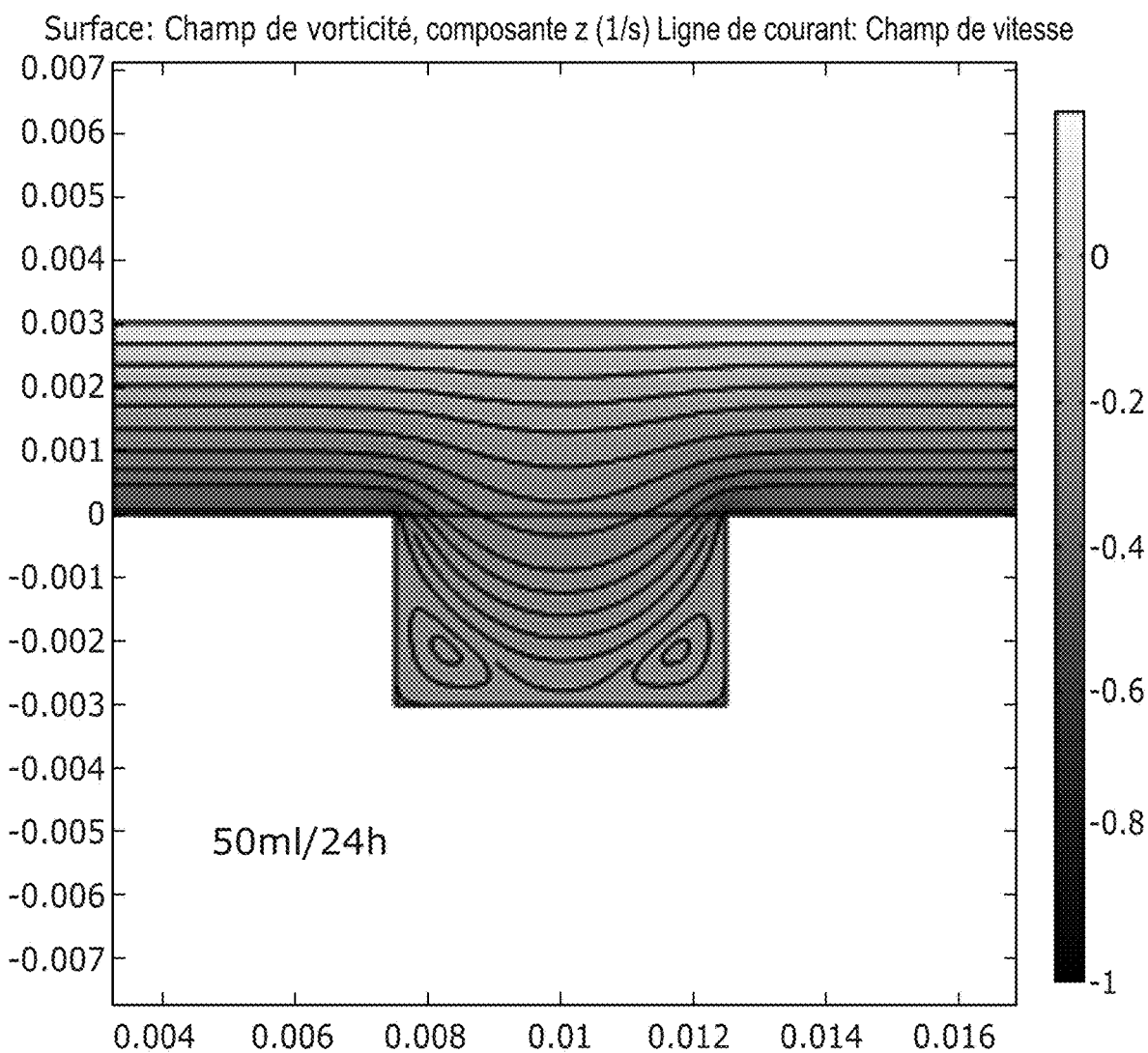
Figure 10C:
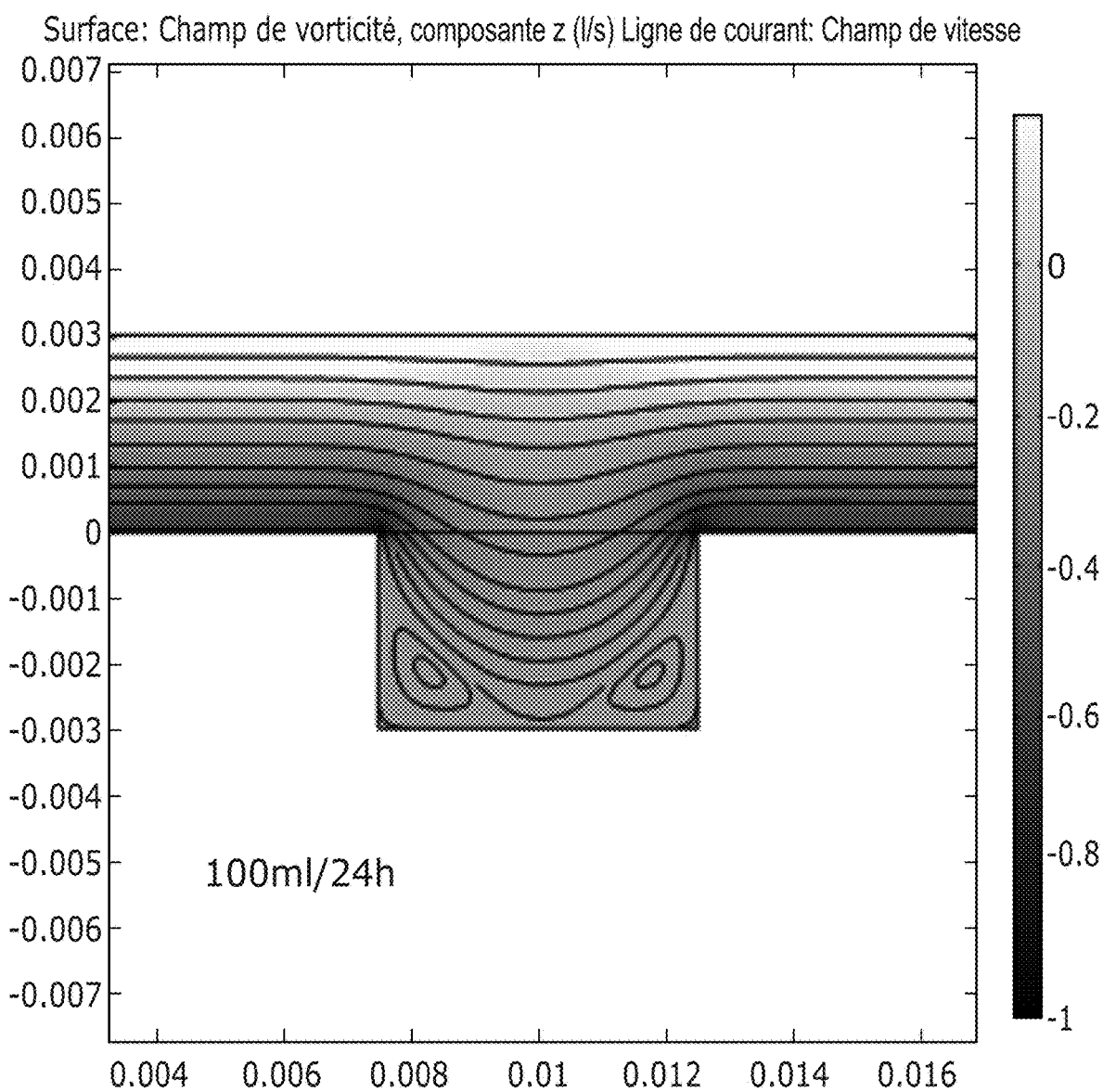
Figure 10D:
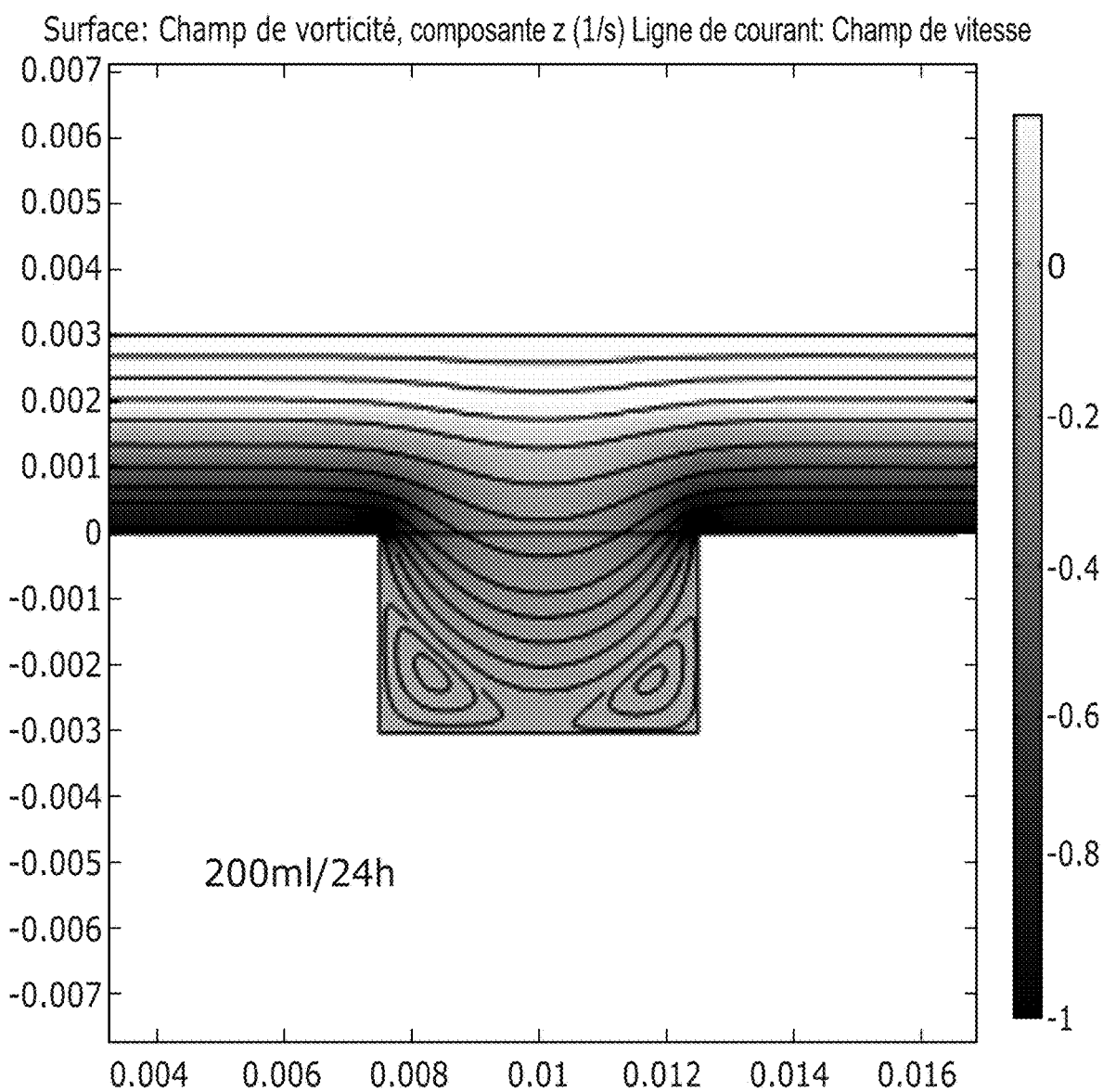
Figure 14:
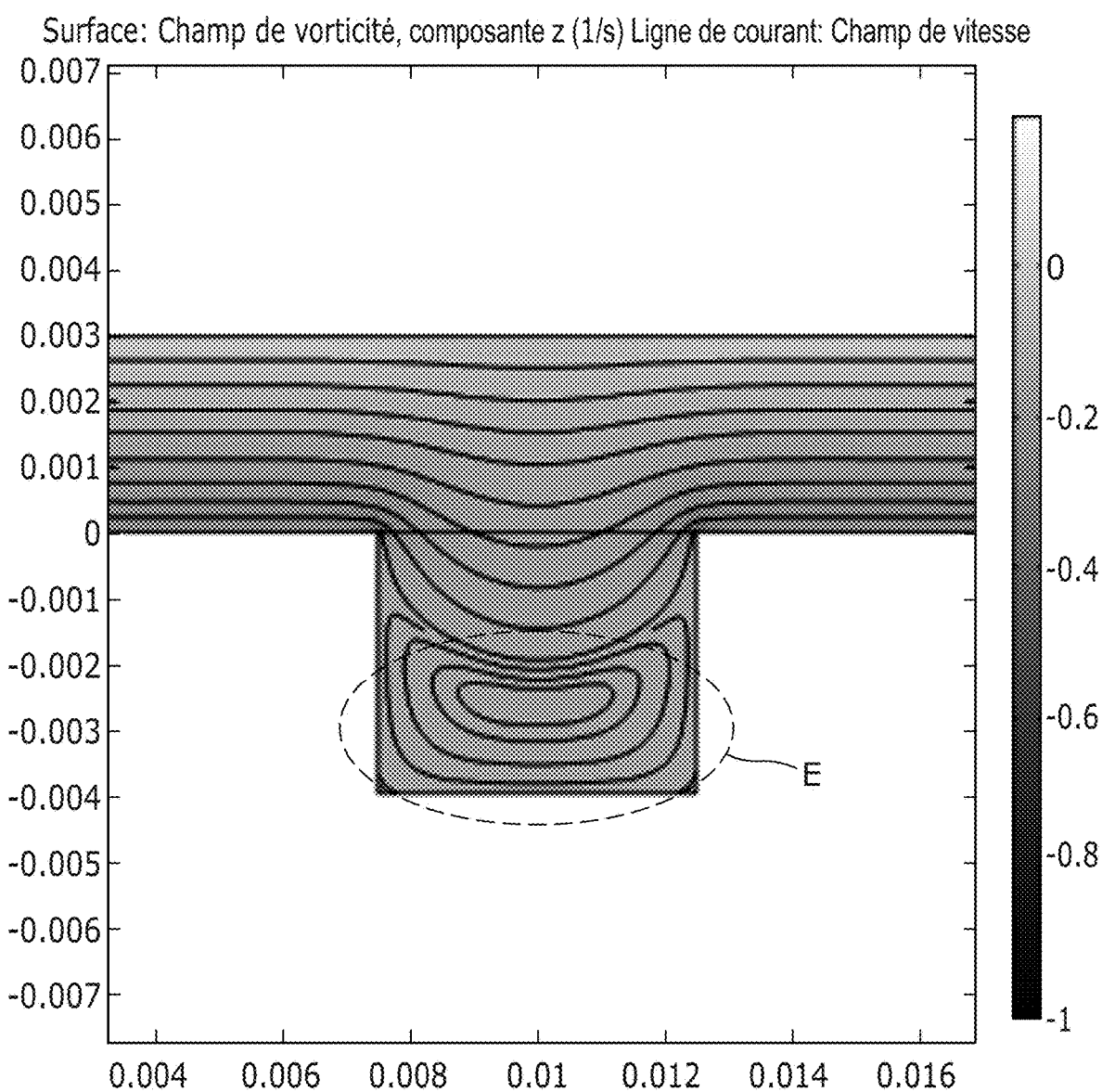
FIG. 14 shows the way in which the length of the vertical limb of the T affects the dead-space size E within the limb.

It has been found, by simulation, that the cavity depth varies the size of the dead space above the membrane which will also have a bearing on the position of the sensors. In FIG. 10a, for example, the dead-space, where there is substantially contained fluid flow, occurs at the two lower corners at regions labeled D. This should be compared with FIG. 14 in which, for a deeper cavity, the dead-flow region E is clearly larger for the same flow rate of 25 ml/24 h. The sensors should be placed higher than the dead-space so they are exposed to continuously refreshed exudate flow.

Example 2

In FIG. 7, an embodiment is shown with a sensor 70 located on a support. The height of the support will be chosen to place it at the optimum position using a similar flow and vorticity analysis as before. In a yet further alternative embodiment, the sensor 70 may also be mounted at an angle to the main flow. That angle may be made adjustable or set to a predetermined angle.

Figure 15A:
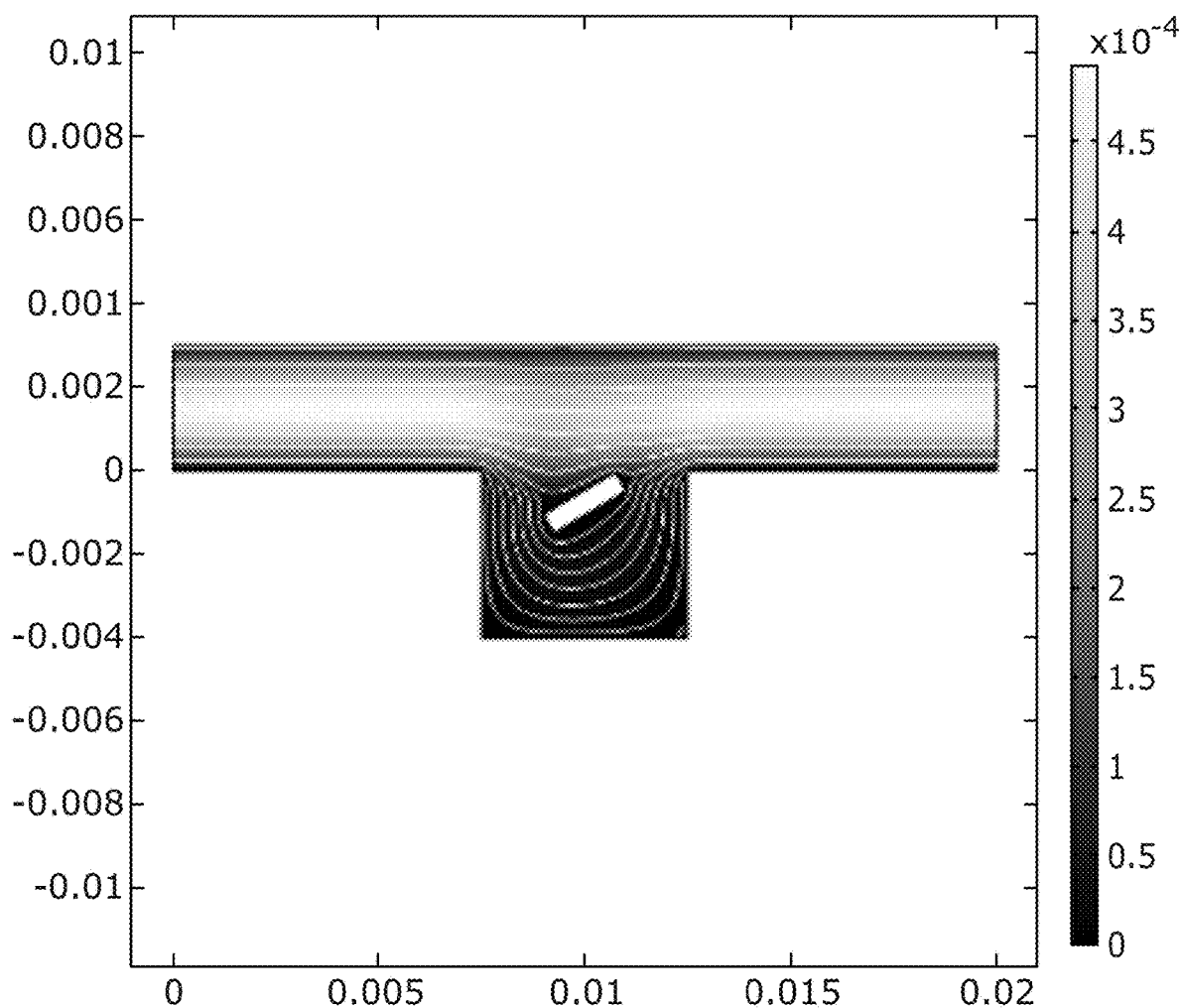
FIGS. 15a-15c show the way in which exudate flow varies as a sensor is angled at varies angles to the longitudinal axis of the drain.
Figure 15B:
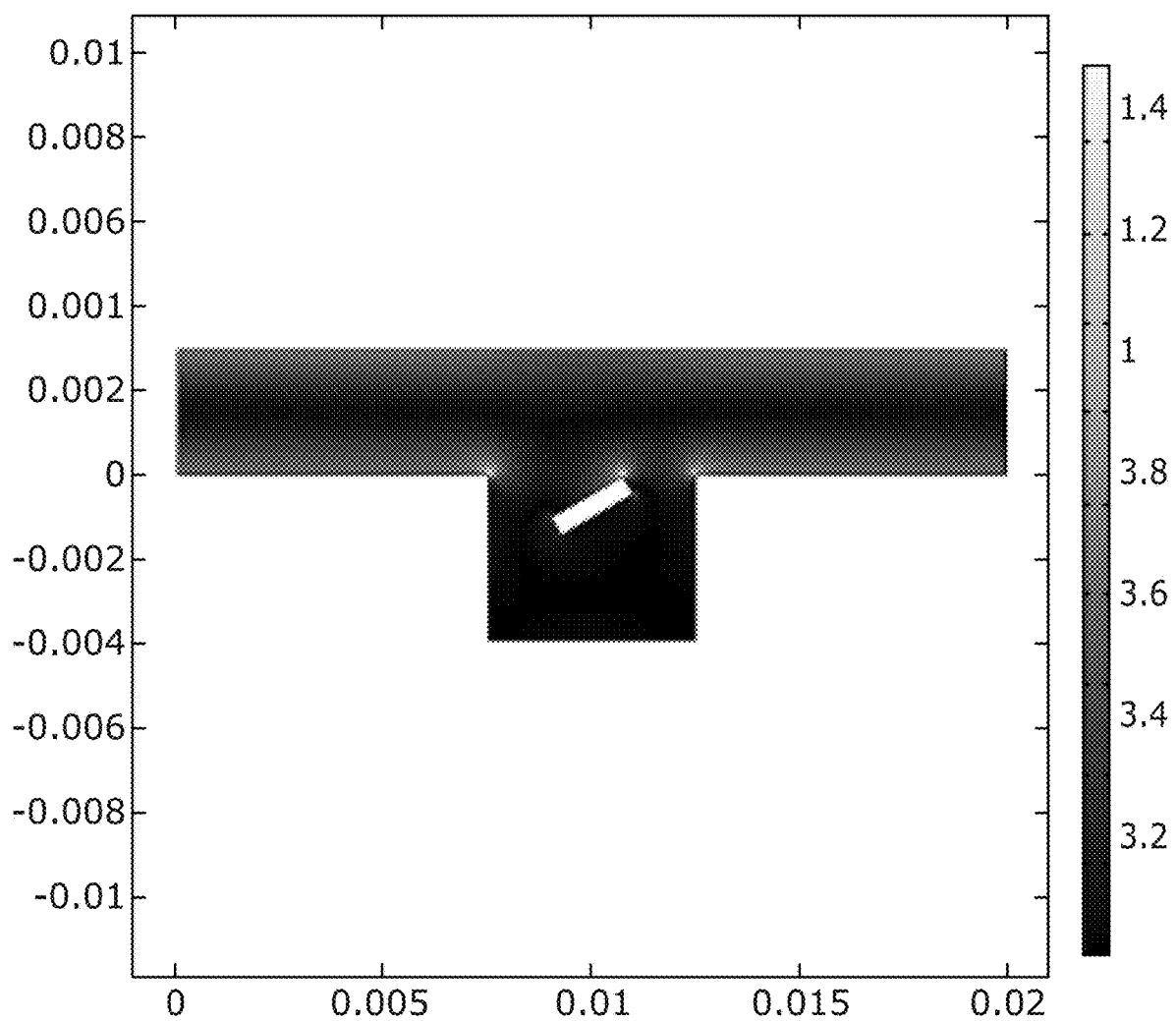
Figure 15C:
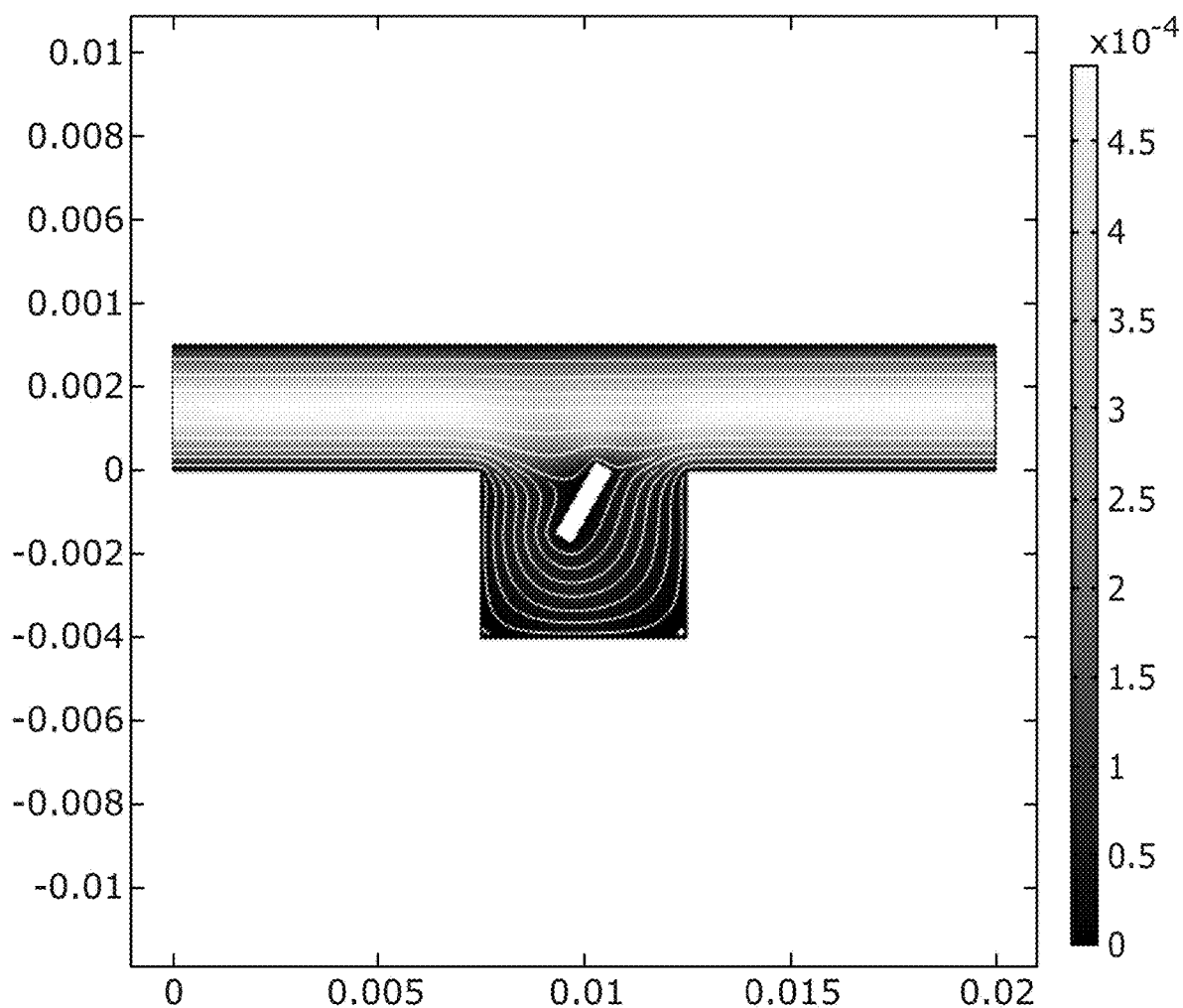

In this example, the optimum angle is determined using the flow analysis with the sensor having a length of 2 mm and thickness of 0.5 mm. In the analysis, the flow is kept at 200 ml/24 hrs as the angle is varied. FIGS. 15a-15c show the resulting flows for the angle being 30 and 60 degrees to the longitudinal axis of the drain. From FIG. 16 it will be seen that the peak vorticity is provided between 30 and 60 degrees with a drop at higher values of angle.

Figure 16:
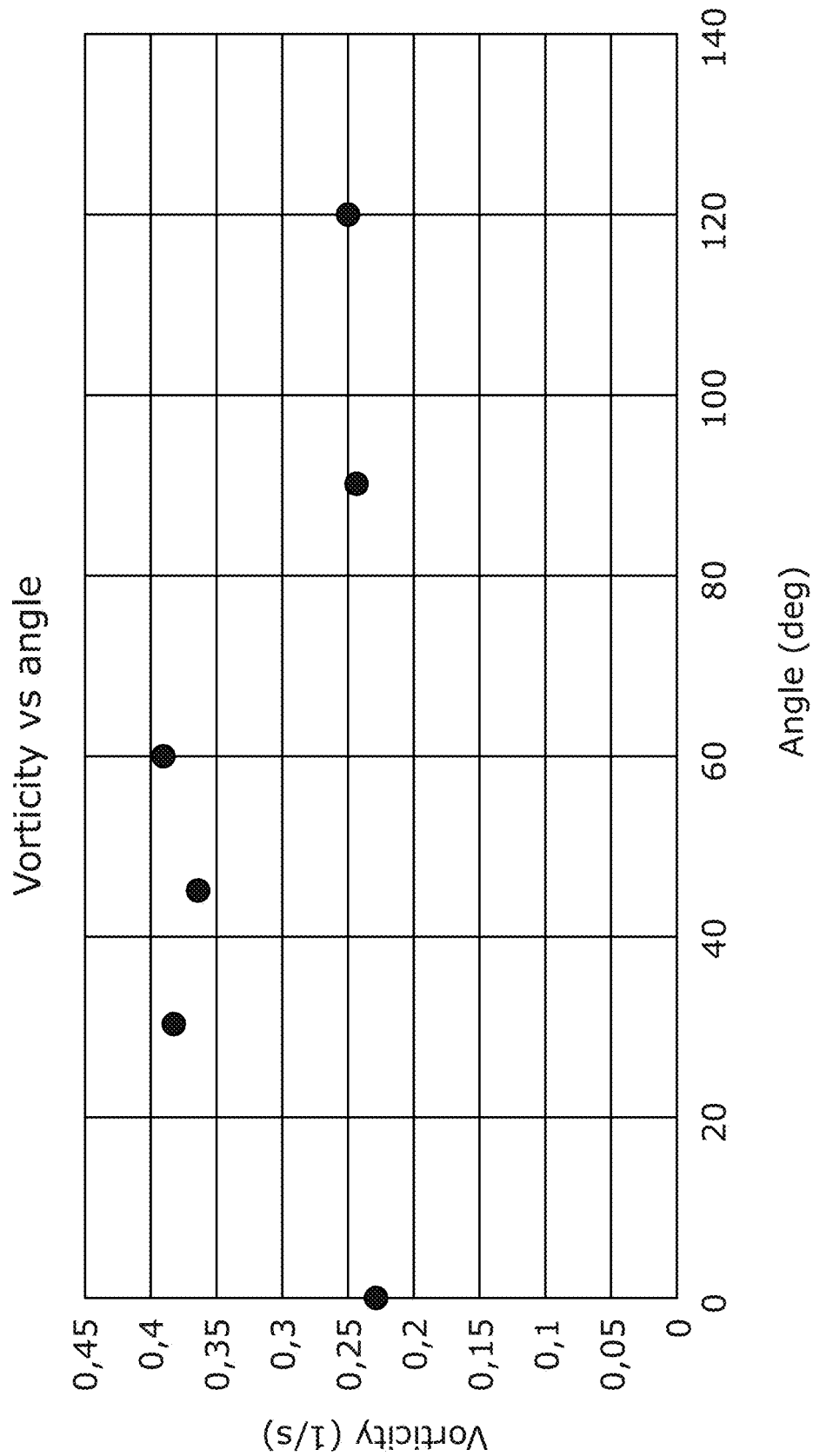
FIG. 16 shows how the vorticity varies with the angles of the sensor shown in FIG. 15.

FIG. 16 shows the average vorticity for different angles of the sensor. The vorticity is averaged from three points taken at the extremities and in the middle of the sensor at 0.1 mm above the surface. There are 3 optimal angles ranging from 30 to 60 deg. From the results of the velocity field and the streamlines, the optimal angle is chosen to be 30 degrees. For 30 degrees, the streamlines show a stagnation point close to the left corner but that should not degrade the sensor measurement if it is centered on the surface.

Figure 17:
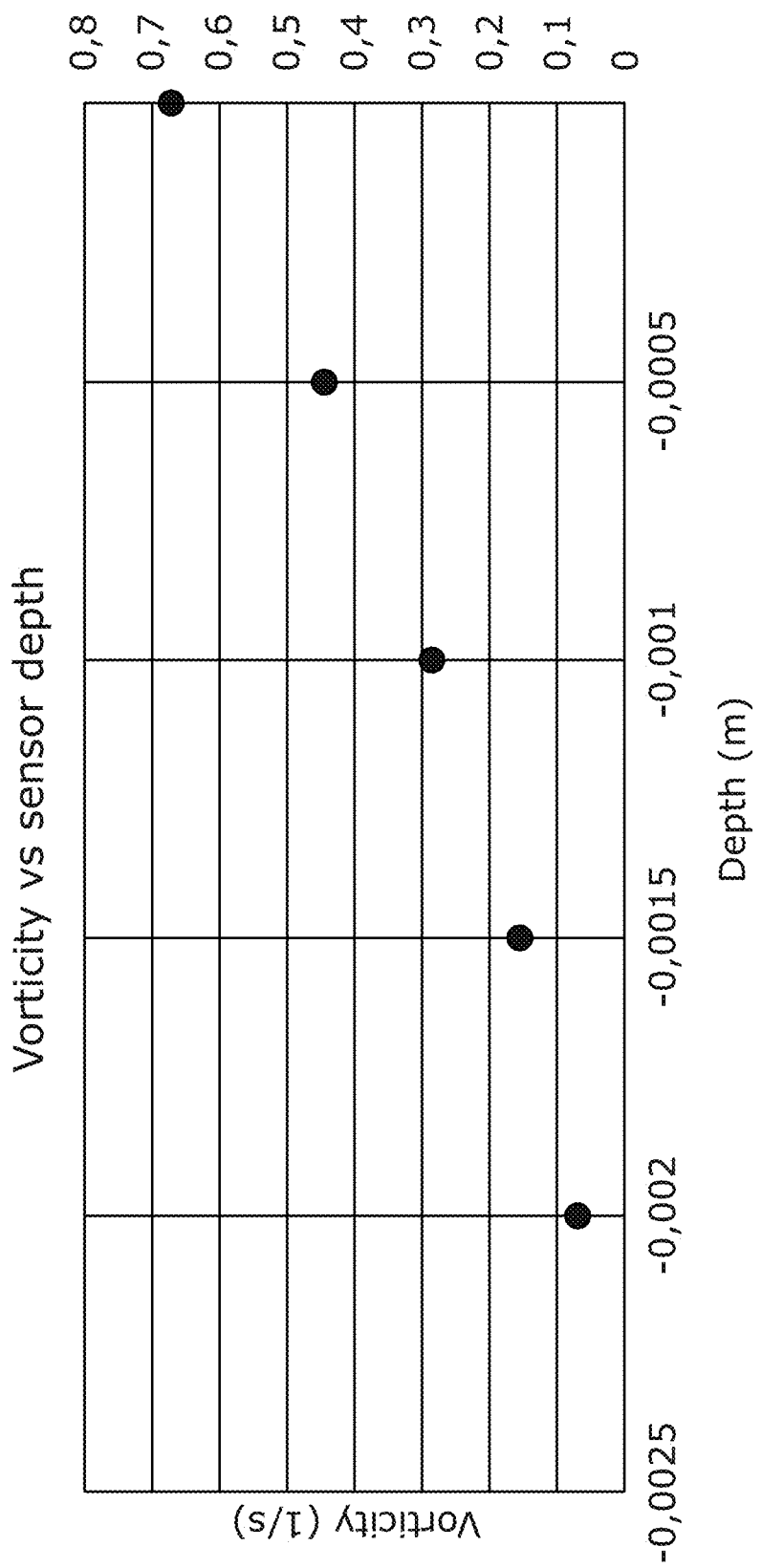
FIG. 17 shows how the vorticity varies with the "depth" of the sensor within the vertical limb of the T of the drain.

FIG. 17 shows how the vorticity varies as the depth of the sensor in the vertical limb of the T or cavity is varied at a constant angle of 30 degrees, that is to say, as the sensor mounting height is lowered from the level of the floor horizontal section of the drain (depth 0 mm on right hand side of the graph). The optimum position is between 0.1 mm and 0.5 mm since this allows good vorticity but also results in there being less potential for blockages caused by the sensor projecting into the main axis of the drain.

Example 3

In this example, an embodiment similar to that shown in FIG. 3 is presented.

Figure 18:
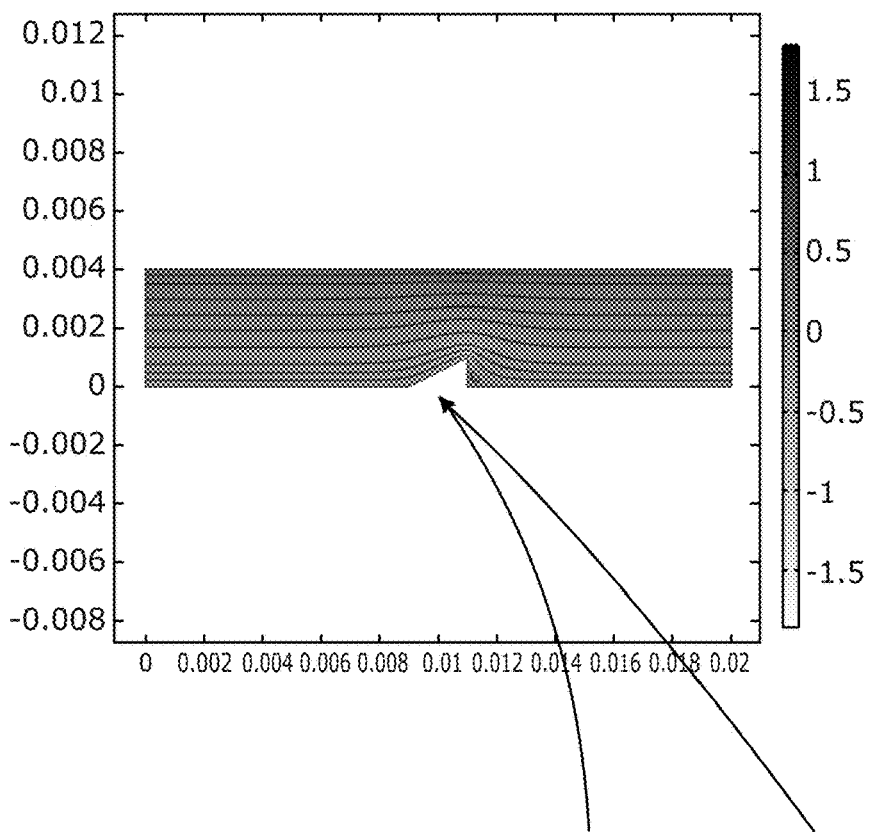
FIG. 18 shows the way in which vorticity varies in the region of a wedge-like step or turbulator in the drain with the lower figure showing an enlarged view of part of the upper.
Figure 18:
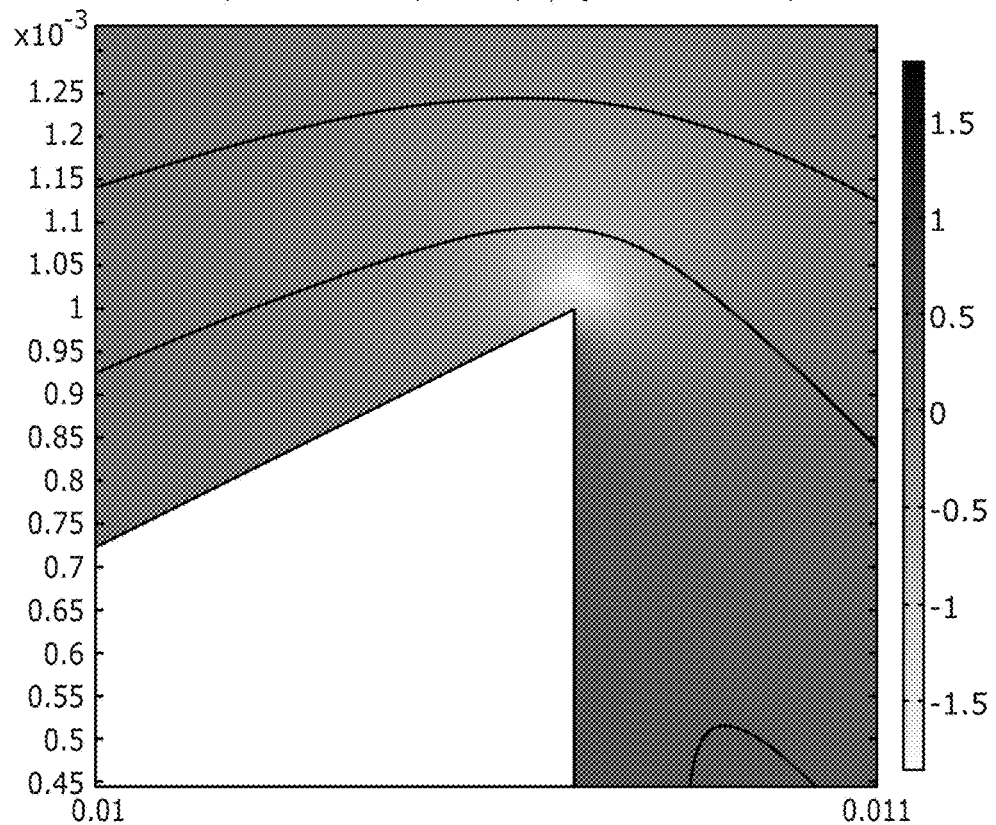

A step is put in the drain to create positions for the mounting of the sensors. An example of a numerical simulation of the flow into a drain (4 mm in diameter) is shown in FIG. 18. The shading indicates the vorticity and the lines the streamlines. The fluid is water and the flowrate is 200 ml/24 h. The step/turbulator is 1 mm high and 2 mm long. The vorticity peak at the end of the step which makes the ideal position to mount the sensor as is the case in FIG. 3.

Figure 19:
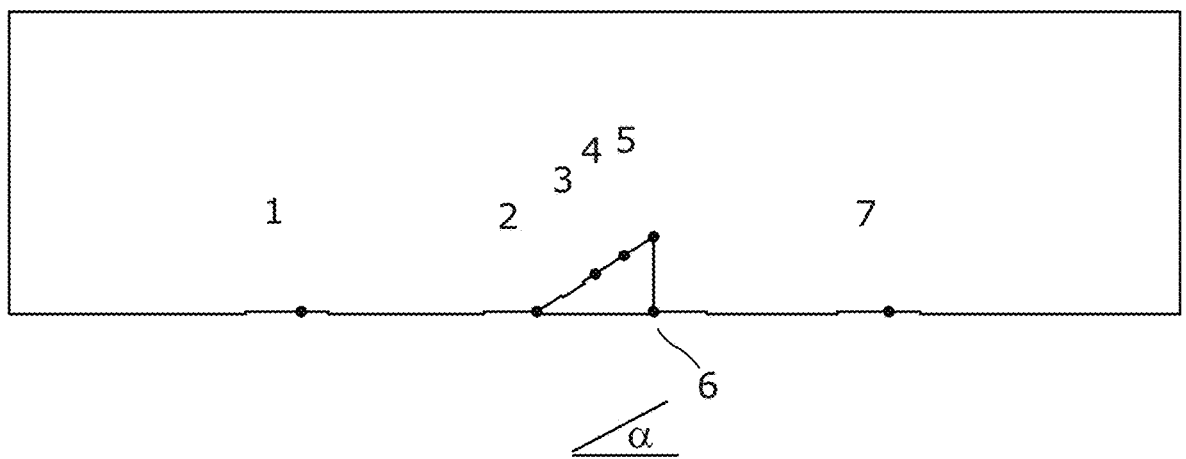
FIG. 19 illustrates various positions for potential location of sensors about the turbulator shown in FIG. 18 to be modelled.
Figure 20:
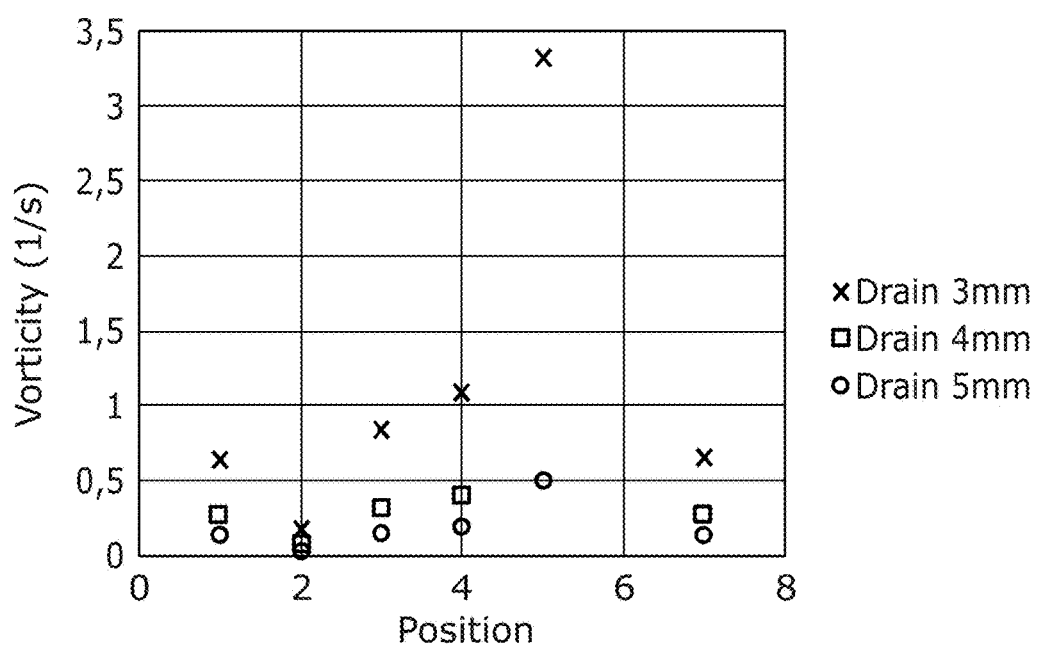
FIG. 20 shows the vorticity at various potential sensor positions shown in FIG. 18 at various diameters of the drain.

FIG. 19 shows a number of positions modelled for flow to further determine the best position for the sensor as the drain diameter is varied to be 3, 4 or 5 mm in diameter with FIG. 20 showing the results. It will be seen that the best location for the sensor will be at position 5 for all the diameters in this embodiment.

Figure 21:
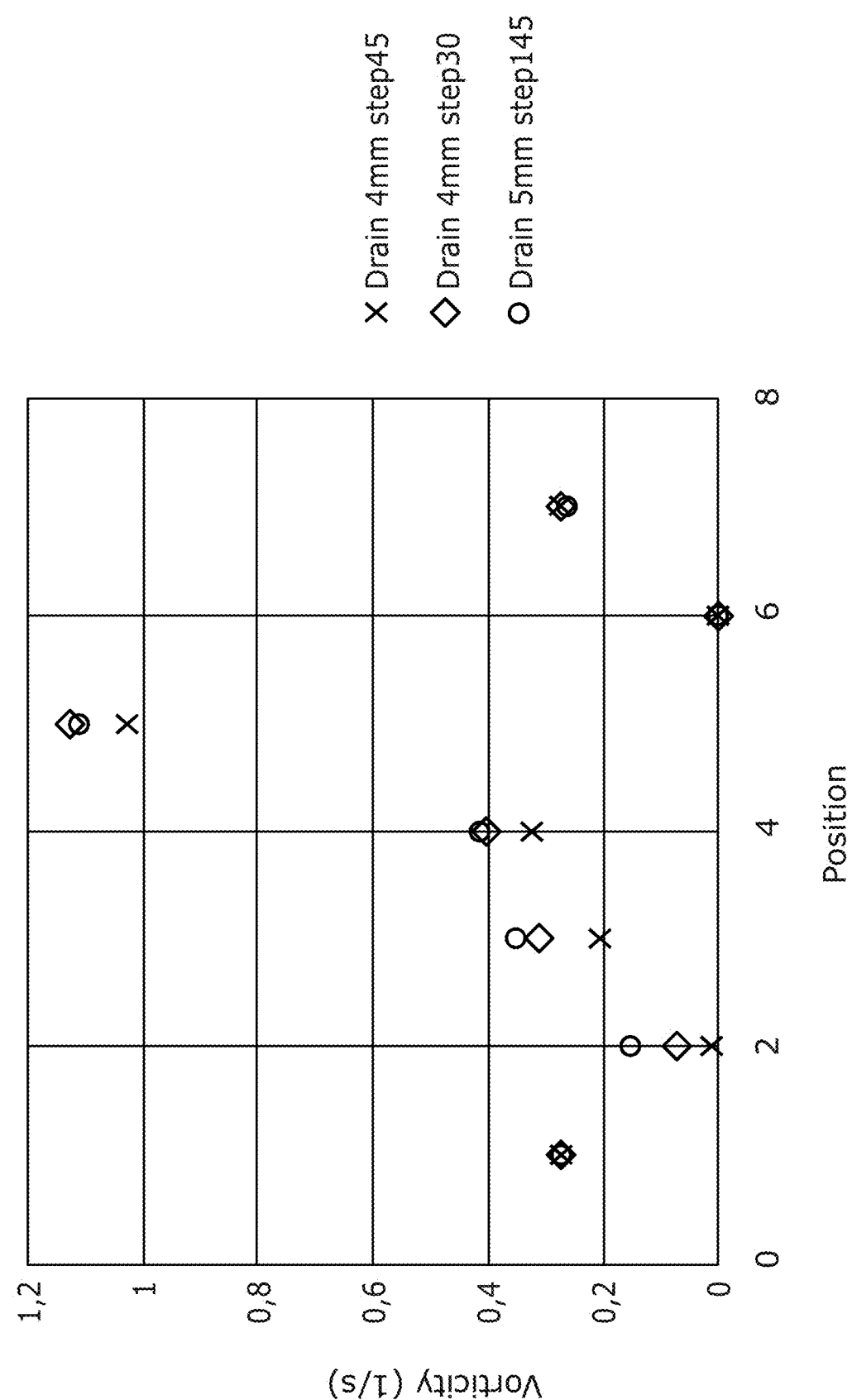
FIG. 21 shows how vorticity varies at the positions in FIG. 19 if the angle of the turbulator shape is varied.

FIG. 21 shows how the vorticity varies as the angle of the step a is varied at the seven positions. Again position 5 at the step edge is the best position with the optimum angle being 14.5 degrees.

The length of the turbulator ramp, or its profile, may be varied using similar considerations.

It will be appreciated that more than one sensor may be placed within the drain, that is to say the above described embodiments may be combined in a number of ways to provide a multisensory embodiment.

Figure 22:
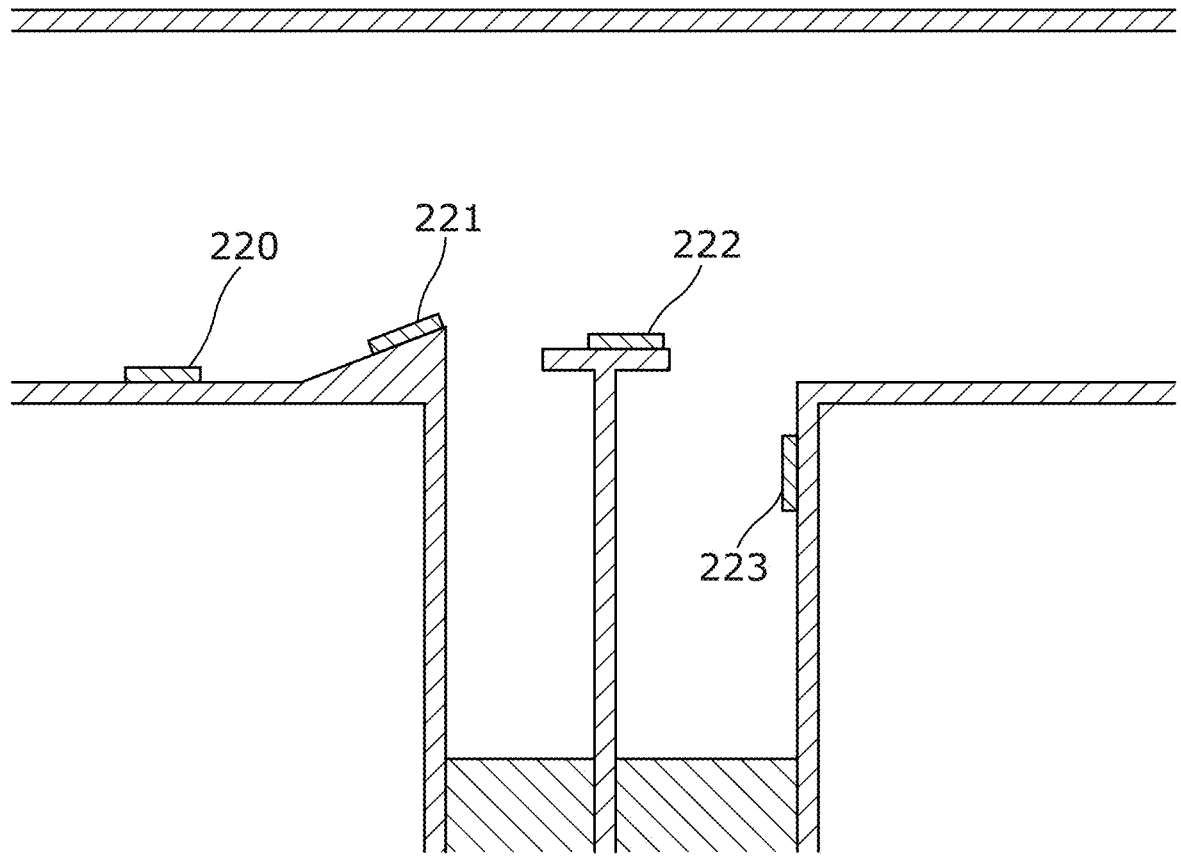
FIG. 22 shows a cross-sectional views of a multiple sensor embodiment of the invention having a number of sensors some of which are located in a drain at regions of re-circulatory flow

FIG. 22 shows a multiple sensor embodiment. In this embodiment, sensors 220, 221, 222 and 223 are placed in various positions in the drain some of which will include positions where there is re-circulatory flow. Their outputs may be monitored in the same manner as described with reference to the system shown in FIG. 1.

What is claimed is:

1. A medical drain for draining exudate from a surgical site, comprising:
   a tube including a first lumen and a second lumen, wherein the first lumen is within a vertical limb of a "T" shaped section of the tube;
   at least one sensor located in the first lumen of the tube and configured to be exposed to exudate flow and located in a region of re-circulatory exudate flow, wherein the at least one sensor is disposed within the first lumen of the tube such that fluid that bypasses the first lumen bypasses the at least one sensor; and
   at least two turbulators disposed within the tube, a first turbulator of the at least two turbulators configured to at least one of provide or enhance a re-circulatory exudate flow and to initially direct its re-circulatory exudate flow away from the at least one sensor, the first turbulator extending in a direction of flow and forming a wedge shape, a second turbulator of the at least two turbulators configured to at least one of provide or enhance a re-circulatory exudate flow and to initially direct its re-circulatory exudate flow toward the at least one sensor,
   wherein each of the first turbulator and the second turbulator includes an inclined face; and
   wherein the second lumen defines a constant internal diameter exclusive of the first turbulator and the second turbulator.

2. The medical drain of claim 1, wherein each of the first turbulator and the second turbulator comprises a projection extending inwardly to a longitudinal axis of the tube from an internal face of the tube.

3. The medical drain of claim 2, wherein the first turbulator projects inwardly by a distance in the range of 1/5 to 1/3 of the internal diameter of the tube.

4. The medical drain of claim 3, wherein the distance is 1/4 of the internal diameter of the tube.

5. The medical drain of claim 1, wherein the first turbulator extends in the direction of flow by a distance in the range of 10% to 0.70% of the internal diameter of the tube.

6. The medical drain of claim 5, wherein the first turbulator extends in the direction of flow by the distance equal to 0.50% of the internal diameter of the tube.

7. The medical drain of claim 1, wherein the inclined face is inclined at an angle to an inner wall of the tube, the angle ranging from 14.5 degrees to 45 degrees.

8. The medical drain of claim 7, wherein the angle ranges from 14.5 degrees to 30 degrees.

9. The medical drain of claim 1, wherein the at least one sensor is a microelectrode sensor or an array of microelectrode sensors.

10. The medical drain of claim 1, wherein the at least one sensor is formed on a substrate positioned on a wall of the tube.

11. The medical drain of claim 1, wherein the at least one sensor is integrally formed on a wall of the tube.

12. The medical drain of claim 1, wherein the at least one sensor is mounted on a removable support located in the vertical limb of the "T" shaped section of the tube.

13. The medical drain of claim 1, wherein the at least one sensor is mounted to provide a sensor surface directed at an angle to a longitudinal axis of the tube.

14. The medical drain of claim 1, wherein the at least one sensor includes a plurality of sensors located at regions of re-circulatory flow.

15. The medical drain of claim 1, wherein the first turbulator and the second tubular are disposed within the second lumen.

16. The medical drain of claim 1, wherein the first lumen has a second constant internal diameter.

* * * * *